United States Patent
Kumagai et al.

(10) Patent No.: US 7,642,362 B2
(45) Date of Patent: *Jan. 5, 2010

(54) COMPOUNDS AS SEMAPHORIN INHIBITORS

(75) Inventors: Kazuo Kumagai, Hyogo (JP); Nobuo Hosotani, Hyogo (JP)

(73) Assignee: Dainippon Sumitomo Pharma Co., Ltd., Osaka-Shi (JP)

( * ) Notice: Subject to any disclaimer, the term of this patent is extended or adjusted under 35 U.S.C. 154(b) by 677 days.

This patent is subject to a terminal disclaimer.

(21) Appl. No.: 10/502,453

(22) PCT Filed: Jan. 22, 2003

(86) PCT No.: PCT/JP03/00567

§ 371 (c)(1), (2), (4) Date: Jan. 12, 2005

(87) PCT Pub. No.: WO03/062243

PCT Pub. Date: Jul. 31, 2003

(65) Prior Publication Data

US 2005/0119334 A1 Jun. 2, 2005

(30) Foreign Application Priority Data

Jan. 24, 2002 (JP) ............................. 2002-015216

(51) Int. Cl.
*C07D 311/92* (2006.01)
*C07D 493/00* (2006.01)
*C07D 311/94* (2006.01)

(52) U.S. Cl. .................. 549/223; 549/224; 549/331; 549/348; 549/354; 549/358; 549/359; 549/381; 549/382; 549/387

(58) Field of Classification Search .............. 549/223, 549/224, 388, 354, 331, 358, 359, 381, 382, 549/387

See application file for complete search history.

(56) References Cited

U.S. PATENT DOCUMENTS 5,229,123 A * 7/1993 Masubuchi et al. ......... 424/408

5,416,197 A 5/1995 Raper et al.
7,244,761 B2 * 7/2007 Kimura et al. ............. 514/455

FOREIGN PATENT DOCUMENTS

| EP | 0 537 622 A1 | 4/1993 |
| WO | WO 92/16517 A1 | 10/1992 |
| WO | WO 98/11216 A1 | 3/1998 |
| WO | WO 98/15628 A1 | 4/1998 |
| WO | WO 02/09756 A1 | 2/2002 |

OTHER PUBLICATIONS

Goshima et al , Jol. Clinical Invest., vol. 109 No. 8 pp. 993-998(2002).*
Kim et al, Expert Opin. Biol. Ther. (2006) vol. 6 No. 8 pp. 735-738.*
Abrahart, Dyes and their Intermediates (1969) pp. 8.*
Goshima Y. et al., "Functions of Semaphorins in Axon Guidance and Neuronal Regeneration," Japan J. Pharmacol., vol. 82(4):273-279, (2000).

* cited by examiner

*Primary Examiner*—Janet L. Andres
*Assistant Examiner*—Raymond Covington
(74) *Attorney, Agent, or Firm*—Venable LLP; Robert Kinberg; Nancy J. Axelrod

(57) ABSTRACT

Compounds represented by the general formula (1)

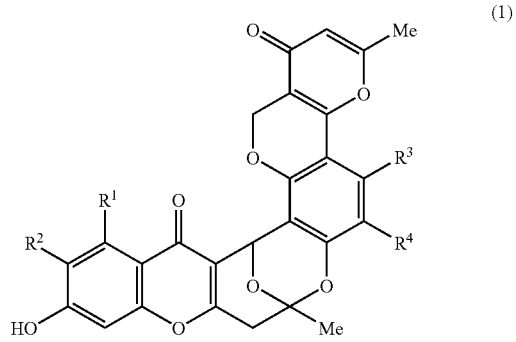

wherein $R^1$ and $R^3$ are each independently hydrogen or a carboxyl group and $R^2$ and $R^4$ are each independently hydrogen or a hydroxyl group, or pharmaceutically acceptable salts thereof, which exhibit semaphorin-inhibitory activity and are useful as preventives or remedies for neuropathic and neurodegenerative diseases are provided.

20 Claims, 8 Drawing Sheets

COMPOUNDS AS SEMAPHORIN INHIBITORS

TECHNICAL FIELD

The present invention relates to a novel compound having semaphorin inhibitory activity, a microbiological process for producing the compound, a nerve regeneration promoter containing the compound as an active ingredient, or the like.

BACKGROUND ART

Nerve cells are special tissues which have no mitotic potential in an adult. Therefore, once they are injured, the damage will last over a long period of time. Particularly, there is no regeneration potential in the central nervous system such as brain and spinal cord. Lack of the regeneration potential in the central nerves can be regarded as one of the reasons that there have been no established therapies for traumatic injuries such as spinal cord injury, nor for neurodegenerative diseases such as Alzheimer's disease and Parkinson disease. On the other hand, peripheral nerves possess regeneration potential. Their axons can regenerate and their functions can be recovered even after having been severed. In this case, however, the recovery requires a long span of time ranging from several months to even more than a year, and thus patients have to undergo considerable sufferings. Moreover, the recovery period is so long that some nerve cells may die during this period, which often leads to the failure of recovery of the functions. And yet, even the peripheral nerves having regeneration potential are entirely unable to outgrow when placed in the central nervous system such as brain and spinal cord. This brings the basis for the hypothesis that there exist some substances in the central nervous system that inhibit nerve outgrowth. If the inhibitory substances for nerve regeneration in the central nervous system are suppressed by using antibodies or the like, nerve regeneration in the central nervous system as well as the recovery of their functions will be observed, even though partially. As one of such inhibitory substances for the central nerve regeneration, Nogo has been recently discovered (Nature 403, 434, 2000, Nature 403, 439, 2000). However, only a small portion of axons are regenerated by inhibiting Nogo and it is thus presumed that there exist some other regeneration-inhibitory substances but up to now, it is still not clear which substances act to inhibit nerve regeneration in vivo.

Referring to semaphorin, its gene was first isolated as a factor involved in nervous system formation in developing locusts. Since then, it has been reported that semaphorins constitute a large gene family distributed in nematodes, fish, mammals and even certain kinds of virus, and currently semaphorin genes are classified into eight gene subfamilies or classes based on their structures (Cell 97, 551, 1999). Semaphorin is an endogenous protein identified as a factor which collapses nerve growth cone and suppresses axon outgrowth, and so far, about 20 molecular species have been reported (Cell 97, 551, 1999). However, most functions of many semaphorin families have not yet been clarified in detail. The most studied gene group is that of a subfamily called class 3, all of whose translation products are secretory proteins. Although proteins encoded by these genes are known to possess intensive neurite outgrowth suppressing activity and growth cone collapse activity in vitro, it was also reported that they can act inductively neurite outgrowth under certain conditions. Of semaphorins, semaphorin 3A (Sema3A) is the most studied and is known to induce growth cone collapse of the cultured nerve cells at as low as 10 pM concentration in a short period of time (Cell 75, 217, 1993, Cell 75, 1389, 1993). In order to analyze in vivo functions of semaphorins, knockout mice for neuropilin-1, which is one of the components of Sema3A receptor, have been studied (Neuron 19, 995, 1997). The knockout mice show embryonic lethality as well as motor abnormality in some nervous systems such as trigeminal nerve and angiogenesis abnormality. Although similar motor abnormality in nervous systems is observed in Sema3A knockout mice, some individual mice are reported to grow up to adults without serious problem. Therefore, the in vivo functions of Sema3A remain largely unknown.

Moreover, with regard to semaphorins the followings are also known: antisense nucleototides and antagonists such as antibodies or the like for semaphorin W, semaphorin Y and semaphorin Z are made for central nerve regeneration promoters (WO98/15628, WO98/11216, WO98/20928); and a method of inducing neurite outgrowth by contacting a nerve cell with an antibody that specifically binds to human collapsin is known (U.S. Pat. No. 5,416,197). However, no low-molecular weight compounds which specifically inhibits semaphorin were completely unknown up to now.

DISCLOSURE OF THE INVENTION

The object of the present invention is to provide a novel compound having a semaphorin inhibitory activity, a microbiological process for producing the compound, a nerve regeneration promoter containing the compound as an active ingredient, or the like.

Semaphorins are thought to have various actions, and some researchers postulated that semaphorins were involved not only in the nerve development but also in the nerve regeneration, but actually nothing was known about that. The present inventors have found that compounds designated as SPF-3059-1 and the like discovered in the culture of *Penicillium* sp. SPF-3059 strain have semaphorin inhibitory activity and have demonstrated that the compounds also promote nerve regeneration in vivo. The present inventors have further found a novel compound having a semaphorin inhibitory activity by isolating and purifying the culture of SPF-3059 strain and screening a substance which inhibits the semaphorin activity in vitro. The present invention was accomplished based on these findings.

Accordingly, the present invention relates to the following:

[1] A compound represented by the general formula (1):

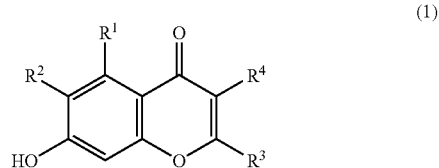

wherein $R^1$ represents a hydrogen atom or a carboxyl group, $R^2$ represents a hydrogen atom or a hydroxyl group, and $R^3$ and $R^4$ represent one of the following [I] to [IX]:

[I] $R^3$ and $R^4$, are joined to form a divalent group of the formula (2):

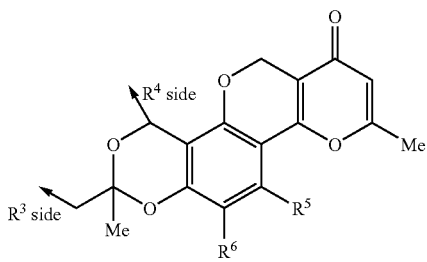

(2)

wherein $R^5$ represents a hydrogen atom or a carboxyl group and $R^6$ represents a hydrogen atom or a hydroxyl group;

[II] $R^3$ and $R^4$ are joined to form a divalent group of the formula (3):

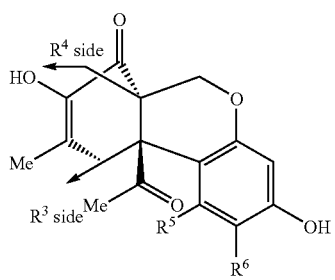

(3)

wherein $R^5$ and $R^6$ have the same meanings as above;

[III] $R^3$ and $R^4$ are joined to form a divalent group of the formula (4):

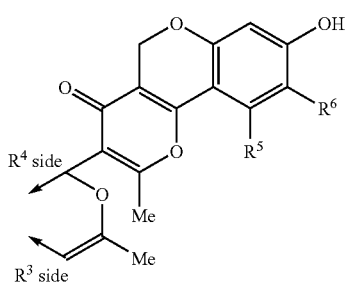

(4)

wherein $R^5$ and $R^6$ have the same meanings as above;

[IV] $R^3$ and $R^4$ are joined to form a divalent group of the formula (5):

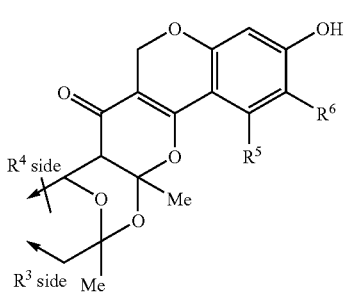

(5)

wherein $R^5$ and $R^6$ have the same meanings as above;

[V] $R^3$ represents a hydrogen atom and $R^4$ represents a group of formula (6):

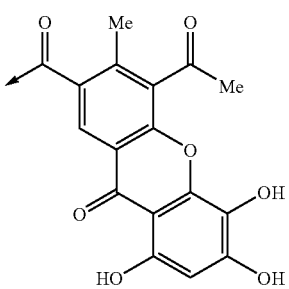

(6)

[VI] $R^3$ and R4 are joined to form a divalent group of the formula (7);

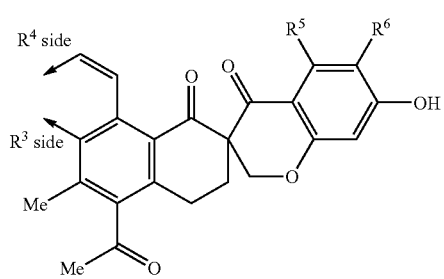

(7)

wherein $R^5$ and $R^6$ have the same meanings as above;

[VII] $R^3$ represents a group of the formula (8):

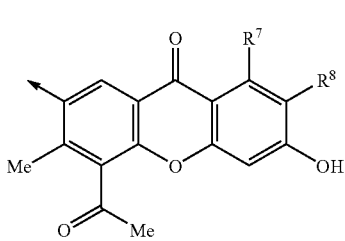

(8)

wherein $R^7$ represents a hydrogen atom or a carboxyl group and $R^8$ represents a hydrogen atom or a hydroxyl group, and $R^4$ represents a group of the formula (9):

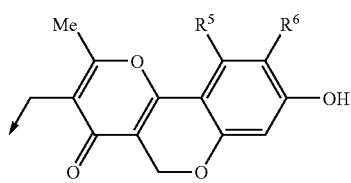
(9)

wherein $R^5$ and $R^6$ have the same meanings as above;

[VIII] $R^3$ and $R^4$ are joined to form a divalent group of the formula (10):

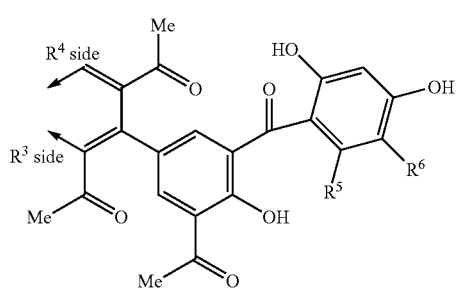
(10)

wherein $R^5$ and $R^6$ have the same meanings as above;

[IX] $R^3$ and $R^4$ are joined to form a divalent group of the formula (11):

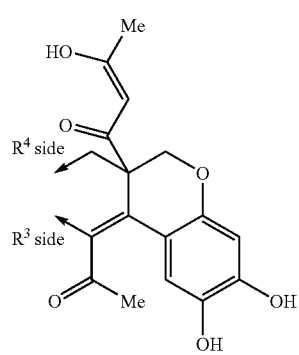
(11)

or a pharmaceutically acceptable salt thereof.

[2] The compound according to [1] represented by the general formula (12):

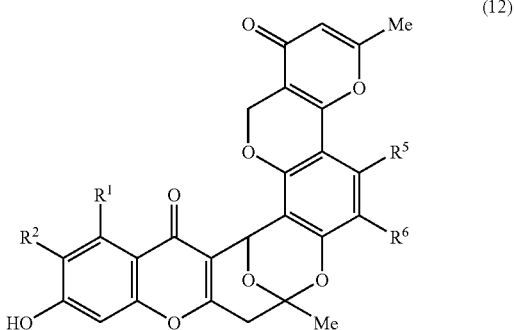
(12)

wherein $R^1$, $R^2$, $R^5$ and $R^6$ have the same meanings as in [1], or a pharmaceutically acceptable salt thereof.

[3] The compound according to [2], wherein $R^1$ and $R^5$ are independently a carboxyl group, $R^2$ is a hydroxyl group or a hydrogen atom and $R^6$ is a hydroxyl group in the general formula (12), or a pharmaceutically acceptable salt thereof.

[4] The compound according to [1] represented by the general formula (13):

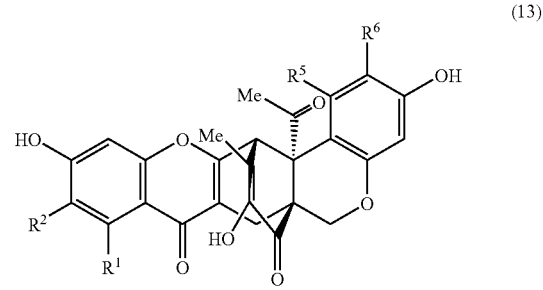
(13)

wherein $R^1$, $R^2$, $R^5$ and $R^6$ have the same meanings as in [1], or a pharmaceutically acceptable salt thereof.

[5] The compound according to [4], wherein $R^1$ and $R^5$ are independently a carboxyl group, and $R^2$ and $R^6$ are independently a hydroxyl group in the general formula (13), or a pharmaceutically acceptable salt thereof.

[6] The compound according to [1] represented by the general formula (14):

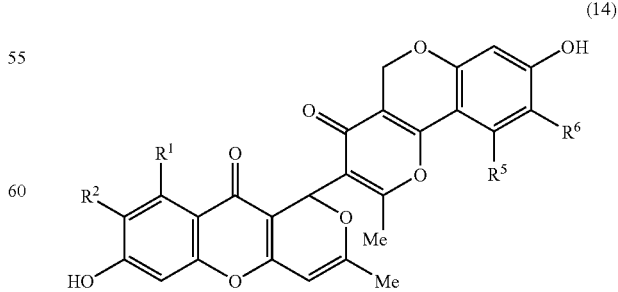
(14)

wherein $R^1$, $R^2$, $R^5$ and $R^6$ have the same meanings as in [1], or a pharmaceutically acceptable salt thereof.

[7] The compound according to [6], wherein $R^1$ and $R^5$ are independently a carboxyl group, and $R^2$ and $R^6$ are independently a hydroxyl group in the general formula (14), or a pharmaceutically acceptable salt thereof.

[8] The compound according to [1] represented by the general formula (15):

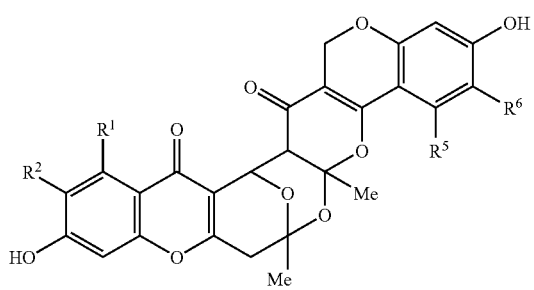

(15)

wherein $R^1$, $R^2$, $R^5$ and $R^6$ have the same meanings as in [1], or a pharmaceutically acceptable salt thereof.

[9] The compound according to [8], wherein $R^1$ and $R^5$ are independently a carboxyl group, and $R^2$ and $R^6$ are independently a hydroxyl group in the general formula (15), or a pharmaceutically acceptable salt thereof.

[10] The compound according to [1] represented by the general formula (16):

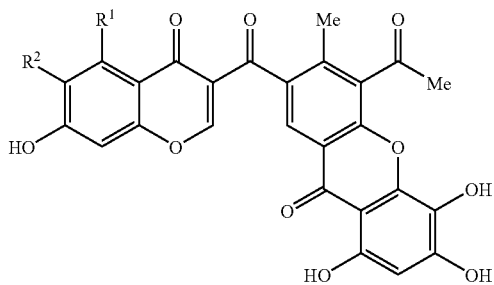

(16)

wherein $R^1$ and $R^2$ have the same meanings as in [1], or a pharmaceutically acceptable salt thereof.

[11] The compound according to [10], wherein $R^1$ represents a carboxyl group and $R^2$ represents a hydroxyl group in the general formula (16), or a pharmaceutically acceptable salt thereof.

[12] The compound according to [1] represented by the general formula (17):

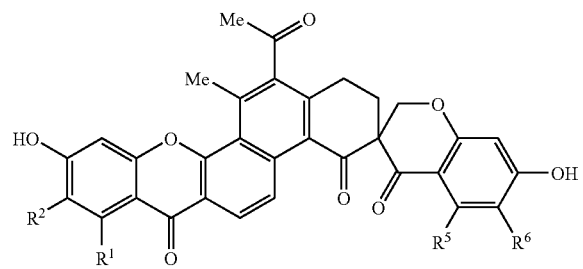

(17)

wherein $R^1$, $R^2$, $R^5$ and $R^6$ have the same meanings as in [1], or a pharmaceutically acceptable salt thereof.

[13] The compound according to [12] wherein $R^1$ and $R^5$ each represents a carboxyl group, and $R^2$ and $R^6$ represent independently a hydroxyl group in the general formula (17), or a pharmaceutically acceptable salt thereof.

[14] The compound according to [1] represented by the general formula (18):

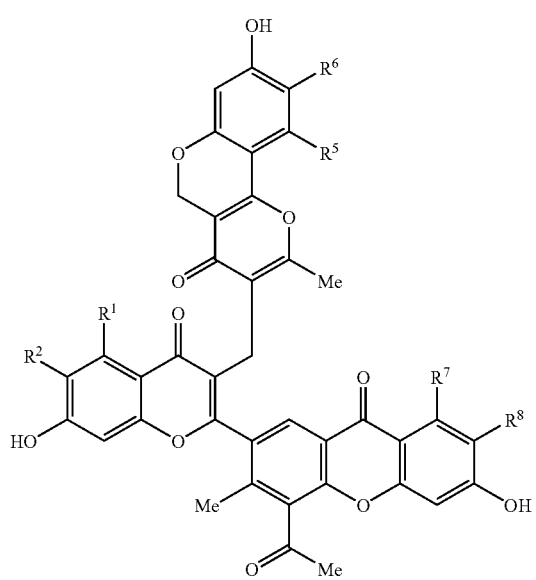

(18)

wherein $R^1$, $R^2$, $R^5$, $R^6$, $R^7$ and $R^8$ have the same meanings as in [1], or a pharmaceutically acceptable salt thereof.

[15] The compound according to [14], wherein $R^1$ and $R^5$ are carboxyl groups, and $R^2$, $R^6$ and $R^8$ are independently a hydroxyl group in the general formula (18), or a pharmaceutically acceptable salt thereof.

[16] The compound according to [15], wherein $R^7$ is a hydrogen atom in the general formula (18), or a pharmaceutically acceptable salt thereof.

[17] The compound according to [1] represented by the general formula (19):

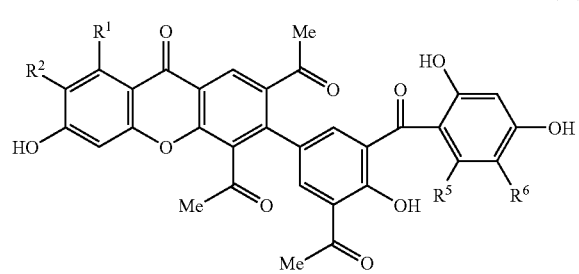

(19)

wherein $R^1$, $R^2$, $R^5$ and $R^6$ have the same meanings as in [1], or a pharmaceutically acceptable salt thereof.

[18] The compound according to [17], wherein $R^2$ and $R^6$ are independently a hydroxyl group in the general formula (19), or a pharmaceutically acceptable salt thereof.

[19] The compound according to [18], wherein $R^5$ is a carboxyl group in the general formula (19), or a pharmaceutically acceptable salt thereof.

[20] The compound according to [19], wherein $R^1$ is a carboxyl group in the general formula (19), or a pharmaceutically acceptable salt thereof.

[21] The compound according to [1] represented by the general formula (20):

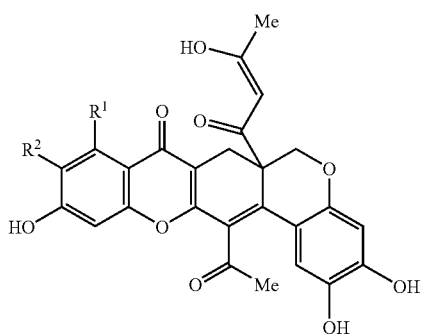

(20)

wherein $R^1$ and R2 have the same meanings as in [1], or a pharmaceutically acceptable salt thereof.

[22] The compound according to [21], wherein $R^1$ is a carboxyl group and $R^2$ is a hydroxyl group in the general formula (20), or a pharmaceutically acceptable salt thereof.

[23] A compound obtainable from SPF-3059 strain which belongs to the genus *Penicillium*, having the following physical and chemical properties and a semaphorin inhibitory activity:
(a) fast atom bombardment mass spectrum m/z value $(M+H)^+$: 545;
(b) molecular formula: $C_{28}H_{16}O_{12}$;
(c) UV-visible absorption spectrum λmax (in methanol) nm(ε): 213 (41700), 286 (29500), 338sh(14900), 429sh (6500);
(d) Infrared absorption spectrum νmax (KBr) $cm^{-1}$: 3358, 3073, 1700, 1674, 1631, 1464, 1276, 1248;
(e) $^1$H-NMR spectrum (DMSO-d6, 500 MHz): spectrum chart shown in FIG. 1;
(f) $^{13}$C-NMR spectrum (DMSO-d6, 125 MHz): spectrum chart shown in FIG. 2.

[24] A compound obtainable from SPF-3059 strain which belongs to the genus *Penicillium*, having the following physical and chemical properties and a semaphorin inhibitory activity:
(a) fast atom bombardment mass spectrum m/z value $(M+H)^+$: 561;
(b) molecular formula: $C_{28}H_{16}O_{13}$;
(c) UV-visible absorption spectrum λmax (in methanol) nm(ε): 219 (34300), 257 (28900), 311 (28600), 404 (14600), 450 (14400);
(d) Infrared absorption spectrum νmax (KBr) $cm^{-1}$: 3154, 1657, 1605, 1468, 1279;
(e) $^1$H-NMR spectrum (DMSO-d6): spectrum chart shown in FIG. 3;
(f) $^{13}$C-NMR spectrum (DMSO-d6): spectrum chart shown in FIG. 4.

[25] A compound obtainable from SPF-3059 strain which belongs to the genus *Penicillium*, having the following physical and chemical properties and a semaphorin inhibitory activity:
(a) fast atom bombardment mass spectrum m/z value $(M+H)^+$: 669;
(b) molecular formula: $C_{34}H_{20}O_{15}$,
(c) UV-visible absorption spectrum λmax (in methanol) nm(ε): 213 (54600), 235sh(39400), 312 (31300), 350 (24200);
(d) Infrared absorption spectrum νmax (KBr) $cm^{-1}$: 3348, 1766, 1707, 1644, 1588, 1464, 1301;
(e) $^1$H-NMR spectrum (DMSO-d6, 500 MHz): spectrum chart shown in FIG. 5;
(f) $^{13}$C-NMR spectrum (DMSO-d6, 125 MHz): spectrum chart shown in FIG. 6.

[26] A compound obtainable from SPF-3059 strain which belongs to the genus *Penicillium*, having the following physical and chemical properties and a semaphorin inhibitory activity:
(a) fast atom bombardment mass spectrum m/z value $(M+H)^+$: 549;
(b) molecular formula: $C_{28}H_{20}O_{12}$,
(c) UV-visible absorption spectrum λmax (in methanol) nm(ε): 227 (30200), 282sh(13500), 315 (13900), 356 (11000);
(d) Infrared absorption spectrum νmax (KBr) $cm^{-1}$: 3396, 1688, 1662, 1622, 1470, 1294;
(e) $^1$H-NMR spectrum (DMSO-d6, 500 MHz): spectrum chart shown in FIG. 7;
(f) $^{13}$C-NMR spectrum (DMSO-d6, 125 MHz): spectrum chart shown in FIG. 8.

[27] A semaphorin inhibitor comprising as an active ingredient the compound according to any one of [1] to [26], or a pharmaceutically acceptable salt thereof.

[28] The semaphorin inhibitor according to [27], wherein the semaphorin is a class 3 semaphorin.

[29] The semaphorin inhibitor according to [28], wherein the class 3 semaphorin is semaphorin 3A.

[30] The semaphorin inhibitor according to [27], wherein the semaphorin is a class 6 semaphorin.

[31] The semaphorin inhibitor according to [30], wherein the class 6 semaphorin is semaphorin 6C.

[32] An inhibitor for a nerve outgrowth repelling factor comprising a semaphorin inhibitor according to any one of [27] to [31], as an active ingredient.

[33] An agent having suppressing action on the growth cone collapse activity and/or on the nerve outgrowth inhibitory activity in a collagen gel comprising a semaphorin inhibitor according to any one of [27] to [31], as an active ingredient.

[34] A nerve regeneration promoter comprising a semaphorin inhibitor according to any one of [27] to [31], as an active ingredient.

[35] A preventive or remedy for neuropathic diseases and/or neurodegenerative diseases, comprising a semaphorin inhibitor according to any one of [27] to [31], as an active ingredient.

[36] A preventive or remedy for diseases including spinal nerve injury and/or peripheral nerve injury, comprising a semaphorin inhibitor according to any one of [27] to [31], as an active ingredient.

[37] A preventive or remedy for olfactory abnormality, traumatic neuropathy, cerebral infractional neuropathy, facial nerve paralysis, diabetic neuropathy, glaucoma, retinitis pigmentosa, Alzheimer's disease, Parkinson's disease, neurodegenerative diseases, muscular hypoplastic lateral sclerosis, Lou Gehrig's disease, Huntington's chorea, cerebral infarction or traumatic neurodegenerative diseases, comprising a semaphorin inhibitor according to any one of [27] to [31], as an active ingredient.

[38] A process for producing a compound or a pharmaceutically acceptable salt thereof according to any one of [1] to [26] wherein a microorganism belonging to the genus *Penicillium* is cultured and that the compound is collected from the culture.

[39] The process for producing a compound according to [38], wherein the microorganism belonging to the genus *Penicillium* is *Penicillium* sp. SPF-3059.

BEST MODE OF CARRYING OUT THE INVENTION

Figure 1:
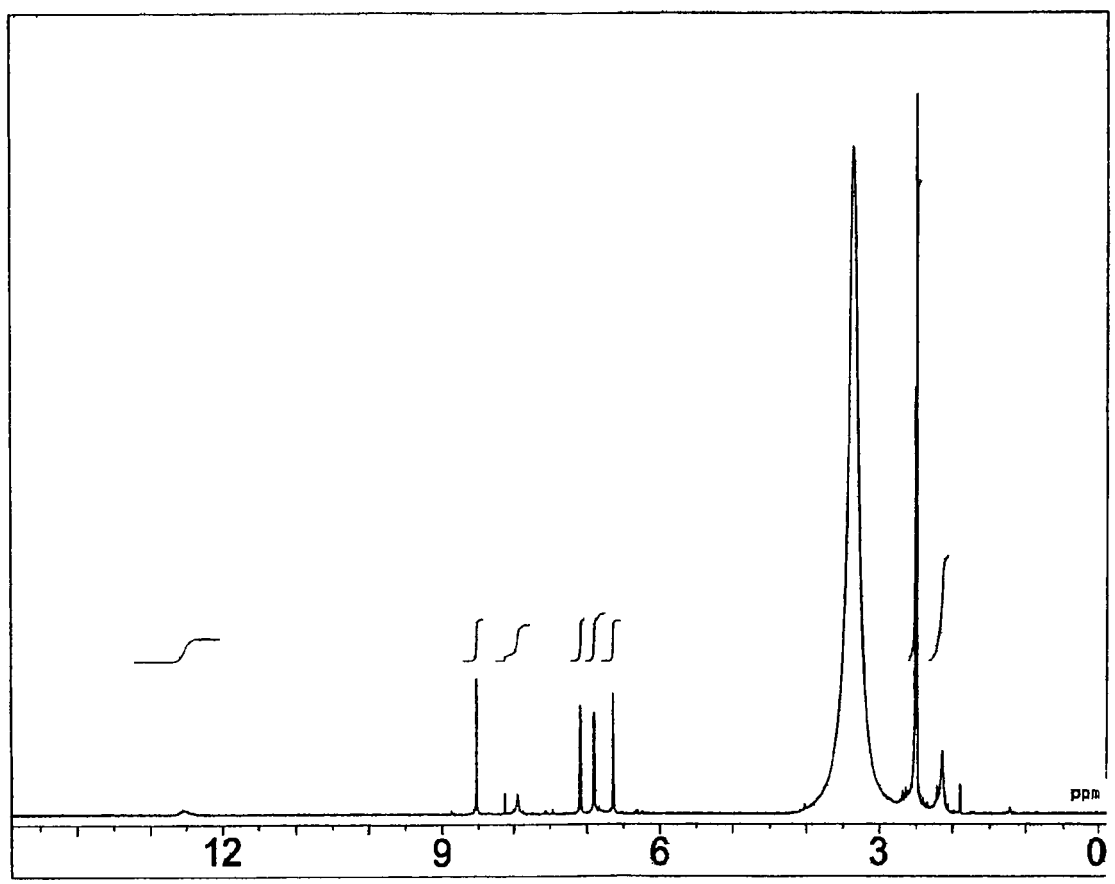
FIG. 1 shows a $^1$H-NMR spectrum (DMSO-$d_6$) of SPF-3059-10.

In the present invention, semaphorin is a generic name for proteins that have semaphorin domains with similar structures consisting of about 500 amino acid residues (Neuron 14, 941-948, 1995), and approximately 20 variants or more have been reported to date. In the present invention, however, semaphorins will not be limited to these publicly known semaphorins. The following can be exemplified as such semaphorins: semaphorins of mammals such as human, etc.; preferably class 3, 4, 5 or 6 semaphorins as defined in the literature (Cell 97, 551, 1999); more preferably class 3 or 6 semaphorins; and most preferably semaphorin 3A (Cell 75, 217, 1993; Cell 75, 1389, 1993) in class 3 semaphorins and semaphorin 6C (WO98/11216, Moll. Cell. Neurosci. 13, 9-23 (1999)) in class 6 semaphorins. Sequence information regarding genes encoding these semaphorins is disclosed in GenBank data base, the aforementioned literatures or the like. Further, semaphorin in the present invention will not be limited to a natural or a recombinant protein but also includes: a protein in which only the extracellular domain of a membrane-bound semaphorin is expressed and solubilized; a fusion protein with other protein such as an antibody, alkaline phosphatase or the like; a protein to which a tag such as His-tag, Flag or the like is added; or a mutant in which part of amino acids are deleted, substituted or added.

For example, semaphorin 6C (Sema6C) is a membrane-bound protein and the extracellular domain of Sema6C is usually used such as for measuring the activity of an inhibitor by utilizing promoting or suppressing actions of Sema6C activities. Two isoforms are known in the extracellular domain of Sema6C (WO98/11216; Moll. Cell. Neurosci. 13, 9-23 (1999)), both of them have the growth cone collapse activity. A fusion protein in which the extracellular domain of said Sema6C and a marker protein and/or a peptide tag are bound can be advantageously used for such cases of measuring the activity of a subject substance as long as the activity of Sema6C is not impaired. Examples of marker proteins include conventionally well known marker proteins such as alkaline phosphatase (Cell 63, 185-194 (1990)), Fc region of an antibody (Genbank accession number M87789), HRP and the like, and peptide tags are exemplified by conventionally well known Mic-tag, His-tag, Flag-tag and the like.

In the present invention, a semaphorin inhibitor means a substance which inhibits an activity of any one of the aforementioned semaphorins such as, for instance, migration activity of a cell, cell death-inducing activity, morphological changes of a cell such as cell rounding or growth cone collapsing, suppressing or promoting activity for neurite outgrowth, suppressing or promoting activity for dendrite outgrowth of nerve cells, nerve axon guidance activity or the like. Any substance inhibiting the foregoing semaphorin activities can be adopted as said semaphorin inhibitor without particular limitation. Preferably, a compound having promoting action on central and/or peripheral nerve regeneration, more preferably a compound having suppressing action on the growth cone collapse activity possessed by semaphorin and/or the nerve outgrowth inhibitory activity in a collagen gel, and even more preferably a compound having suppressing action on both growth cone collapse activity and nerve outgrowth inhibitory activity of semaphorin in a collagen gel are exemplified.

The promoting action on the central and/or peripheral nerve regeneration refers to an action which promotes nerve regeneration in the central nervous tissues such as brain, spinal cord and the like, and/or in the peripheral nervous tissues which are in organs on body surface or in the body that consist the marginal and peripheral portions and not the central nervous tissues. Here, promoting action on the central nerve regeneration includes promoting action not only on the nerve regeneration wherein an axon emerges from a nerve cell body in the central region, such as a retinal nerve or a cerebral cortex nerve, and is projected on other nerve cell which is also in the central region, but also on the nerve regeneration wherein a nerve axon is regenerated in the central nervous tissue circumstance even when a nerve, such as an afferent fiber of an olfactory nerve or a dorsal root ganglion sensory nerve, emerges from a nerve cell body in the peripheral. Further, promoting action on the peripheral nerve regeneration includes promoting action not only on the nerve regeneration of a nerve which emerges from a peripheral nerve cell body and extends in a peripheral tissue, but also on the nerve regeneration wherein the circumstance for regeneration is the peripheral nervous tissue even when a nerve is emerged from a central nerve cell body (brain, spinal cord or the like). The latter can be exemplified by the nerve-regeneration promoting action for such as a spinal cord motor nerve, a preganglionic nerve in the autonomic nervous systems like sympathetic and parasympathetic nerves, and the like. Promoting action on regeneration of a nerve such as a sciatic nerve, which has both nerves mentioned above, can also be exemplified. A compound with promoting action on the central and peripheral nerve regeneration is particularly preferable for a semaphorin inhibitor of the present invention. The central nervous tissue described earlier refers to a tissue comprising brain, medulla oblongata, spinal cord, eye and the like, and more particularly refers to a region where the transport of high-molecular weight substances is restricted by structures such as the blood-brain barrier and the blood-retina barrier. The peripheral nervous system (tissue) refers to the region of the other parts of the body. Nerve fibers are in general capable of regenerating in the peripheral nervous tissues, but they are unable to regenerate in the central nervous tissues.

The growth cone collapse activity of semaphorin described above means an activity to make growth cones disappear. This activity is observed after performing the following steps: cultivating nerve cells (generally tissue explants of ganglions) for a given period of time in vitro until the extended neurites as well as the growth cones at the edge of said neurites can be observed; and then adding thereto a given concentration (e.g. about 3 unit/ml; 1 unit/ml is defined as a semaphorin concentration in which 50% of the growth cones are collapsed) of semaphorin and cultivating for another given period of time (e.g. one hour). In order to get the extended neurites and the growth cones at the edge of said neurites ready for the observation, the nerve cells are generally cultivated for 10 to 20 hours in vitro, which duration can be altered according to a nerve variant and culture conditions. When the growth cone collapse caused by semaphorin is suppressed by, for example, the addition of a compound to this experimental system at an appropriate concentration about one hour prior to the addition of semaphorin, then such compound is regarded as a semaphorin inhibitor, especially as a compound with suppressing action on the growth cone collapse activity of semaphorin. Although there is no particular limitation to a compound with such suppressing action on the growth cone collapse activity, compounds can be exemplified which exhibit the suppressing action at a concentration of 100 µg/ml or less, preferably 30 µg/ml or less, more preferably 10 µg/ml or less, and most preferably 3 µg/ml or less. Further, a compound which does not substantially affect proliferation of the cells such as nerve cells, semaphorin-expressing cells or the like is preferable as a semaphorin inhibitor in order to confirm the effect of semaphorin inhibitors of the present invention and in view of safety when used as a pharmaceutical.

The nerve outgrowth inhibitory activity of semaphorin in a collagen gel as-described above means, for instance, the neurite outgrowth inhibitory activity observed in a collagen gel which contains, for example, both semaphorin-producing cells and nerve cells (usually ganglions). And suppressing action of said neurite outgrowth inhibitory activity is an activity to persistently inhibit the semaphorin activity in a collagen gel, and, for instance, is an activity by which neurites can outgrow to the side of semaphorin-producing cells as much as ½ or more of the outgrowth observed at the opposite side in the presence of the object substance under the experimental condition where neurites can only outgrow up to ⅓ or less to semaphorin producing cells compared with the growth observed at the opposite side of the semaphorin-producing cells when observed after cultivating semaphorin-producing cells and nerve cells adjacently in a collagen gel, usually for overnight or even longer. Further, there is no particular limitation to a compound with suppressing action on the neurite outgrowth inhibitory activity of semaphorin in said collagen gel. However, those exhibiting the foregoing suppressing action at a concentration of 100 µg/ml or less, preferably 30 µg/ml or less, more preferably 10 µg/ml or less and most preferably 3 µg/ml or less are exemplified.

Semaphorin used for measuring the two types of semaphorin activities mentioned above is not limited to a natural semaphorin and the following semaphorins described earlier can be used as well: semaphorin in which only the extracellular domain of a membrane-binding semaphorin is expressed and solubilized; a fusion protein with other protein such as an antibody, alkaline phosphotase or the like; semaphorin to which a tag such as a His-tag or a Flag is added; or semaphorin in which some amino acids are altered. Further, dorsal root ganglions from chick embryos of 7 or 8 embryonic days are conveniently used as-nerve cells for the culture. However, dorsal root ganglions of animals other than chicks, or any other nerve cells such as sympathetic ganglions, retinal ganglions, superior cervical ganglions or the like other than dorsal root ganglions may also be used as long as the nerve cells are capable of extending their neurites in the in vitro culture. There is no particular limitation to the culture condition as long as neurite outgrowth can be observed and semaphorin activities can be measured.

The action mechanism of the semaphorin inhibitors of the present invention can be considered as follows. The neurite outgrowth inhibition or the growth cone collapse caused by semaphorin is triggered by binding of semaphorin to its receptor on the nerve cell surface (growth cone). The signal is transmitted from the receptor to which semaphorin is bound to the intracellular signaling pathway and depolymerization of actin fibers is finally raised, which as a result gives rise to the neurite outgrowth suppression and the growth cone collapse. Inhibition of semaphorin activity is achieved by inhibiting or blocking any of the steps in the course of these reactions. As the above-mentioned receptor for semaphorin, a receptor for any of the foregoing semaphorins may be adopted, and a mutant or a component of a part of such receptor may also be adopted provided that semaphorin can bind to it. Specific examples thereof are Neuropilin-1, plexin and the like (WO01/405457). The semaphorin inhibitors of the present invention will not be restricted by their action mechanisms and an inhibitor which inhibits any one of the steps in the above-described action mechanism is included in the category of the present invention. That is to say, a compound is also included in the category of the present invention, when the compound inhibits semaphorin activity by inhibiting the reactions concerning the intracellular signaling pathway which takes place from the aforementioned receptor-binding of semaphorin to the depolymerization of actin fibers. Besides, a method of measuring the receptor-binding inhibitory activity of semaphorin can be any method if appropriately selected by those skilled in the art, which is exemplified by a method of measuring the receptor-binding inhibitory activity of semaphorin wherein semaphorin fused with other protein such as an antibody, alkaline phosphatase or the like or semaphorin to which His-tag, Flag or the like is added, as described earlier, is bound to a receptor of said semaphorin or to a cell which expresses a receptor component in the presence of a subject substance.

In the general formulae (1) and (12) to (20), $R^1$ represents a hydrogen atom or a carboxyl group and preferably a carboxyl group, and $R^2$ represents a hydrogen atom or a hydroxyl group and preferably a hydroxyl group.

In the general formulae (1), (12) to (15) and (17) to (19), $R^5$ represents a hydrogen atom or a carboxyl group and preferably a carboxyl group, and $R^6$ represents a hydrogen atom or a hydroxyl group and preferably a hydroxyl group.

In the general formula (18), $R^8$ represents a hydrogen atom or a hydroxyl group and preferably a hydroxyl group.

Compounds which constitute semaphorin inhibitors of the present invention can be exemplified by the compounds described later in the Examples in this description.

A compound represented by any of the above-mentioned general formulae (1) and (12) to (20), or a pharmaceutically acceptable salt can be obtained, for example, from the culture of *Penicillium* sp. SPF-3059 with the semaphorin inhibitory activity as an index. The strain was isolated by the present inventors from a soil sample collected in Osaka Prefecture, Japan.

The strain SPF-3059 possesses the following taxomonical characteristics (a) Cultural and Morphological Characteristics On malt extract agar, colonies grow slowly attaining a diameter of 2.8 to 2.9 cm in 21 days at 25° C. The colony surfaces are white to yellow and floccose in appearance and the reverse side color is dark yellow. Neither soluble pigment production nor spore formation is observed. On potato dextrose agar, colonies grow slowly attaining a diameter of 3.2 to 3.3 cm in 21 days at 25° C. The colony surfaces are white to cream yellow and floccose in appearance and the reverse side color is dark yellow to brown. Neither soluble pigment production nor spore formation is observed. On Czapek agar, colonies grow slowly attaining a diameter of 3.1 to 3.2 cm in 21 days at 25° C. The colony surfaces are white to gray and floccose in appearance and the reverse side color is cream yellow. Neither soluble pigment production nor spore formation is observed. On oatmeal agar (Actino Medium No. 3 "DAIGO", Nihon Pharmaceutical Co., Ltd.), colonies grow slowly attaining a diameter of 2.0 to 2.1 cm in 21 days at 25° C. The colony surfaces are white to yellow or grayish green and floccose in appearance and the reverse side color is cream yellow to gray. Soluble pigment is not produced but conidia formation is observed. The conidiophores are smooth-walled with a length of 5 to 20 μm, and generated 3 to 6 phialides in a monoverticillate manner at the end of the conidiophores. On the top of the phialides, which have a length of 3 to 4 μm, conidia are formed in a chain form, with 2 to 10 conidia per chain. The conidia are globose with a diameter of 2.2 to 2.4 μm with striated surface (in general, 10 longitudinal lines on the surface). Teleomorph is not observed.

(b) Physiological Characteristics (1) pH Range for Growth

Growth was examined in shaking culture using Sabouraud broth. Observation was made after cultivation for 3 days at 27° C. The results are as follows:

| pH | Growth |
| --- | --- |
| 3.1 | − |
| 4.5 | + |
| 5.5 | ++ |
| 7.1 | +++ |
| 8.0 | ++ |
| 9.0 | ± |
| 10.0 | − |

(2) Temperature Range for Growth

Growth was observed on an oatmeal agar medium after incubation for 5 days at 38° C.

Based on the above taxonomical characteristics, the strain was identified as a strain of the genus *Penicillium* and was named *Penicillium* sp. SPF-3059. The strain was deposited on Mar. 2, 2000, to the International Patent Organism Depositary of the National Institute of Advanced Industrial Science and Technology, Ibaraki-ken 305-8566 Japan, an Independent Administrative Institution, Japan under the accession number FERM BP-7663 as the International Deposition Number under the Budapest Treaty on the international recognition of the deposit of microorganisms for the purpose of patent procedure.

According to the present invention, nutrient medium for the fermentation of the above-mentioned strain SPF-3059 may either be liquid or solid. Shaking culture or submerged culture with aeration is preferable. No particular limitations are imposed on the medium composition for use. Examples of suitable carbon sources are glucose, sucrose, glycerin, starch, dextrin, molasses or the like. Examples of suitable nitrogen sources are protein hydrolyzate such as peptone and casamino acids; meat extract, yeast extract, soy bean flour, cotton seed flour, corn steep liquor, amino acids such as histidine or the other organic nitrogen sources, ammonium salts, nitrate salts or the other inorganic nitrogen sources. Inorganic elements such as various phosphate salts, magnesium sulfate, sodium chloride, potassium chloride, calcium carbonate can also be added to adjust osmotic pressure, adjust pH, supplement trace elements or the like. Moreover, various additives such as vitamins and nucleic acid related compounds may be added for promoting the growth of the strain. It is also possible to add an antifoam agent such as silicon oil, polypropylene glycol derivative and soy bean oil during the culture period. A preferred temperature range for the culture is preferably 20 to 35° C., more preferably 25 to 30° C., and preferable pH of the medium is, for instance, those ranging around neutral, and the culture period is, for instance, a span of 5 to 10 days.

For isolation and purification of the semaphorin inhibitors of the present invention represented by any of the above-mentioned formulae (1) and (12) to (20) from the fermentation broth, there may be adopted any conventional methods adopted for isolation and purification of secondary metabolites produced by microorganisms. For the isolation and purification of the object compound from the supernatant of the fermentation broth, any of those conventional isolation and purification methods adopted for isolation and purification from the culture filtrate, for example, solvent extraction, ion-exchange chromatography, adsorption chromatography, partition chromatography, gel filtration chromatography, high-performance liquid chromatography (HPLC), thin layer chromatography and the like may be used. These isolation and purification methods may be adopted either alone or in combination. For the isolation and purification of the object compound from the cultured mycelium, the mycelium can be collected by such means as filtration or centrifugation and can be extracted directly by using a water-soluble organic solvent such as acetone, methanol or the like. Then a compound of interest can be obtained from the extract by the similar methods described for isolation and purification from the supernatant of the fermentation broth. Said compound of interest also can be converted to a salt adding an equivalent amount of base in a solvent such as water, methanol, ethanol, acetone, ethyl acetate, chloroform, ether or the like.

In the compounds which constitute semaphorin inhibitors of the present invention, salts thereof, preferably pharmaceutically or veterinary pharmaceutically acceptable salts, are also included in the category of the present invention. The examples of salts include: inorganic basic salts such as sodium salt, potassium salt, calcium salt, magnesium salt, aluminum salt, ammonium salt; organic basic salts such as triethylammonium salt, triethanolammonium salt, pyridinium salt, diisopropylammonium salt; basic amino acid salts such as arginine salt, lysine salt.

There is no specific limitation as to the preventives and remedies of the present invention for neuropathic diseases and/or neurodegenerative diseases including spinal nerve injury and/or peripheral nerve injury, as long as they contain the nerve regeneration promoters described earlier which have an inhibitor for a nerve outgrowth repelling factor, particularly the above-mentioned semaphorin inhibitors, as an active ingredient. Various ingredients such as pharmaceutically acceptable ordinary carriers, binders, stabilizers, excipients, diluents, pH buffers, disintegrating agents, solubilizers, dissolving coadjuvants, isotonic agents may be added. Besides, these preventives and remedies can be administered either orally or parenterally. In other words, they can be administered in usual administration modes, for example, they can be orally administered in agent forms such as powder, granule, capsule, syrup, suspension liquid, or they can be parenterally administered by injecting in agent forms such as solution, emulsion, and suspension. Alternatively, they can be nasally administered in the form of spray agents.

Although dosage and frequency of administration differ depending on the method of administration and the age, weight, medical conditions or the like of a patient, it is preferable to locally administer to the site of disease. Since it takes several days to more than several months for nerves to regenerate, the preventives or remedies are preferably administered once or more than twice during that period to suppress semaphorin activities. When administering twice or more, it is preferable to administer the preventives or remedies repeatedly for consecutive days or at appropriate intervals. Dosage may be defined as several hundred µg to 2 g per administration in form of a semaphorin inhibitor, preferably several dozen mg or less. In order to reduce the administration frequency, sustained release agents, an osmotic pump or the like may be used. In any of these administration methods, it is preferable to adopt an administration route and method wherein the concentration should reach the sufficient level to inhibit semaphorin activity at the site of action.

The above-mentioned neuropathic diseases and/or neurodegenerative diseases including spinal nerve injury and/or peripheral nerve injury include injury or degenerative diseases of peripheral or central nerves enumerated by: olfactory abnormality due to aging or the like; nerve injury other than the olfactory caused by trauma such as spinal cord injury; nerve damage due to cerebral infarction or the like; facial nerve paralysis; diabetic neuropathy; glaucoma; retinitis pigmentosa;, neurodegenerative diseases such as Alzheimer's disease, Parkinson's disease and ALS; muscular hypoplastic lateral sclerosis; Lou Gehrig's disease; Huntington's chorea; cerebral infarction; traumatic neurodegenerative diseases; and so on. Diseases accompanied with angiogenesis in which VEGF165 is involved are also the targets, since VEGF165 also uses neuropilin as its receptor.

In addition, application of the nerve regeneration promoters of the present invention will not be limited to pharmaceuticals such as preventives or remedies for neuropathic diseases and/or neurodegenerative diseases, but are also capably applied to veterinary drugs, or further to industrially important experimental reagents as semaphorin signaling inhibitors. Because they contain semaphorin inhibitors as an active ingredient, nerve regeneration promoters of the present invention promote regeneration of olfactory nerve which is a peripheral nerve, and promote regeneration of nerves in the central region, which are olfactory bulb, cerebral cortex, hippocampus, corpus striatum, thalamus, diencephalon, mesencephalon, cerebellum, pons, medulla oblongata, spinal cord, retina and the like, which are sectioned by blood-cerebrospinal barrier.

EXAMPLES

The present invention will be explained in detail with reference to the examples in the following. The technical scope of the invention, however, will not be limited to these examples.

Example 1

Production of the Compound According to the Present Invention

A volume of 10 ml of a liquid medium containing 2% glucose, 5% sucrose, 2% cotton seed powder, 0.1% sodium nitrate, 0.1% L-histidine, 0.05% dipotassium phosphate, 0.07% potassium chloride and 0.0014% magnesium sulfate heptahydrate, with its pH adjusted to 7.0, was dispensed to a 50-ml Erlenmeyer flask and sterilized in an autoclave. A loopful of *Penicillium* sp. SPF-3059 (FERM BP-7663) on slant culture was inoculated into this medium and cultured with rotary and shaking at 180 rpm for 4 days at 27° C. as the pre-pre-culture. A medium with the same composition as the above-mentioned medium was dispensed 125 ml each to five 500-ml Erlenmeyer flasks and sterilized in an autoclave. Subsequently, 4 ml of the above-mentioned pre-pre-culture solution was added to each of these flasks, which were then cultured with rotary and shaking at 180 rmp for 4 days at 27° C. as the pre-culture. Thirty liters of a liquid medium containing 1.43% glucose, 3.57% sucrose, 1.43% cotton seed powder, 0.07% sodium nitrate, 0.07% L-histidine, 0.036% dipotassium phosphate, 0.05% potassium chloride, 0.001% magnesium sulfate heptahydrate and 0.01% Adekanol LG-295S (antiforming agent by Asahi Denka Co., Ltd.), with its pH adjusted to 7.0, was dispensed into a 50-liters jar fermentor and sterilized under high-pressure steam (121° C., 20 min). Then 500 ml of the above-mentioned pre-culture solution was added to the fermentor and cultured at 27° C. for 9 days with an agitation of 400 rpm and an aeration of 15 liters/min.

After the cultivation, the culture solution was centrifuged at 10,000 rpm for 10 minutes to separate the supernatant and the mycelium. The mycelium fractions were extracted with 30 liters of acetone, then filtered and concentrated. After concentrated into an aqueous solution, it was extracted twice with 10 liters of ethyl acetate-formic acid (99:1). The extract was concentrated under reduced pressure to obtain 130 g of crude extract. The extract was then dissolved into 200 ml of methanol and applied to a column chromatography with Sephadex® LH-20 (Amersham Pharmacia Biotech, Ltd.), and eluted with methanol. Active fractions were collected and the solvent was evaporated under reduced pressure to obtain 91.4 g of oily material. This crude material was then dissolved in 200 ml of methanol for a column chromatography using TOYOPEARL® HW-40F (Tosoh Corporation) and eluted with methanol. The active fractions were collected and the solvent was evaporated under reduced pressure to obtain 41.9 g of crude substance. This crude substance was then dissolved per 500 mg aliquots in 2.5 ml of dimethyl sulfoxide (DMSO) for a preparative reversed-phase HPLC. The conditions of the preparative reversed-phase HPLC were, column: Wakopak® Wakosil-II5C18HGPrep (connecting φ5×10 cm and φ5×25 cm, Wako Pure Chemical Industries, Ltd.), solution A: 1% aqueous formic acid solution, solution B: methanol, gradient:

a linear gradient for 2 hours from 45% to 75% for the proportion of the solution B, flow rate: 25 ml/min, detection: absorbance at 260 nm. The eluted fractions for each one minute were collected.

The eluted fractions as described above were analyzed by analytical HPLC. The conditions of the analytical HPLC were, column: Wakopak® Wakosil-II5C18RS (φ4.6×150 mm, Wako Pure Chemical Industries, Ltd.), solution A: 1% aqueous formic acid solution, solution B: methanol, gradient: a linear gradient for 71.1 min from 20% to 67% for the proportion of the solution B, flow rate: 1.3 ml/min, and detection: absorbance at 260 nm. The fractions containing the object compound were collected with the retention time in this analytical HPLC as the index, and the solvent was evaporated under reduced pressure. The resulting material was again applied to the preparative HPLC and purified in a similar manner as in the above, and were further applied to a column chromatography using TOYOPEARL® HW-40F (Tosoh Corporation) and purified similarly as in the above. Fractions containing the object compound were collected and the solvent was evaporated under reduced pressure, and dried. Thereby, the purified compounds described below were obtained.

TABLE 1

| compound | amount obtained (mg) | retention time in the analytical HPLC (min) |
| --- | --- | --- |
| SPF-3059-8 | 11.1 | 51.2 |
| SPF-3059-10 | 3.3 | 54.8 |
| SPF-3059-16 | 6.7 | 41.5 |
| SPF-3059-17 | 7.9 | 57.0 |
| SPF-3059-18 | 1.6 | 51.5 |
| SPF-3059-19 | 7.8 | 39.6 |
| SPF-3059-20 | 1.3 | 45.5 |
| SPF-3059-22 | 1.0 | 48.4 |
| SPF-3059-23 | 16.7 | 33.2 |
| SPF-3059-31 | 6.5 | 49.6 |
| SPF-3059-38 | 4.0 | 63.1 |
| SPF-3059-40 | 2.3 | 53.7 |
| SPF-3059-41 | 1.0 | 54.0 |
| SPF-3059-42 | 2.4 | 48.2 |

Physicochemical properties of the compounds obtained are as follows:
(SPF-3059-8)
Appearance: yellow powder
Molecular weight: 578
Molecular formula: $C_{28}H_{18}O_{14}$
Fast Atom Bombardment Mass Spectrum (FAB-MS) m/z (positive):
579 $(M+H)^+$
Fast Atom Bombardment Mass Spectrum (FAB-MS) m/z (negative):
576 $(M-H)^-$
High Resolution Fast Atom Bombardment Mass Spectrum (HRFAB-MS) m/z$(M+H)^+$
  Measured value: 579.0779
  Calculated value: 579.0775 ($C_{28}H_{19}O_{14}$)
UV-VISIBLE Absorption Spectrum λmax (in methanol) nm (ε):
  220 (45700), 305 (18200), 358 (16800)
Infrared Absorption Spectrum νmax (KBr) $cm^{-1}$:
  3414, 1652, 1568, 1464, 1614, 1289
  $^1$H-NMR (DMSO-$d_6$) δppm: 1.75 (3H, s), 2.21 (3H, s), 3.06 (1H, d, 18.8), 3.41 (1H, d, 18.8), 4.72 (1H, d, 13.6), 5.02 (1H, d, 13.6), 6.16 (1H, s), 6.17 (1H, s), 6.84 (1H, s) $^{13}$C-NMR (DMSO-$d_6$) δppm:

18.7, 26.9, 38.2, 62.0, 62.1, 101.1, 102.1, 104.8, 112.3, 112.6, 113.3, 113.5, 116.6, 119.1, 119.4, 141.4, 143.7 (2C)) 145.0, 149.9, 152.0, 154.7, 159.4, 164.6, 167.3, 167.7, 170.9, 174.8

Solubility:
  Insoluble in water and hexane, and soluble in methanol and DMSO.

Taken together, the structure of SPF-3059-8 was determined as the following formula:

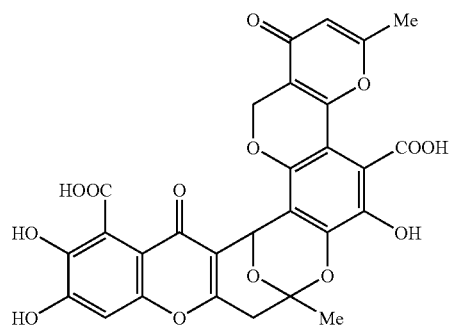

Figure 2:
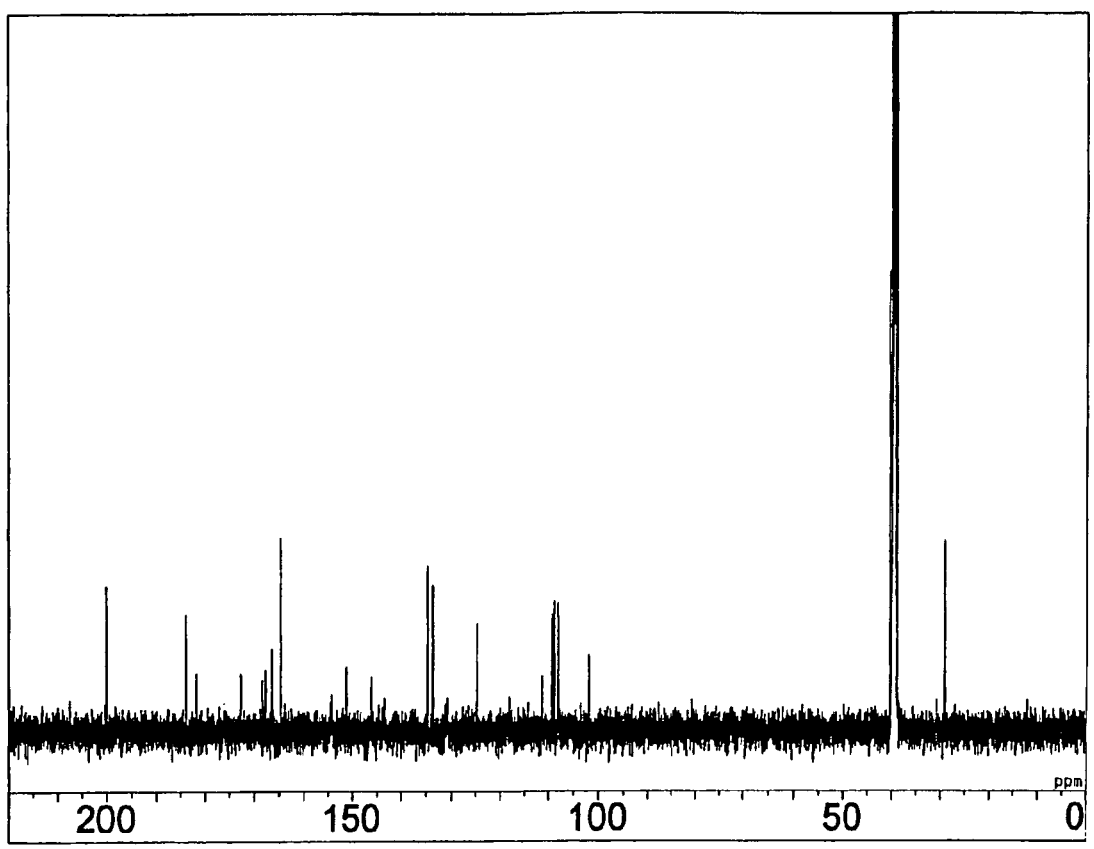
FIG. 2 shows a $^{13}$C-NMR spectrum (DMSO-$d_6$) of SPF-3059-10.

(SPF-3059-10)
Appearance: yellow powder
Properties of the substance: acidic substance
Molecular weight: 544
Molecular formula: $C_{28}H_{16}O_{12}$
Fast Atom Bombardment Mass Spectrum (FAB-MS) m/z (positive):
545 $(M+H)^+$
Fast Atom Bombardment Mass Spectrum (FAB-MS) m/z (negative):
543 $(M-H)^-$
High Resolution Fast Atom Bombardment Mass Spectrum (HRFAB-MS) m/z$(M+H)^+$:
  Measured value: 545.0732
  Calculated value: 545.0740 ($C_{28}H_{17}O_{12}$)
UV-VISIBLE Absorption Spectrum λmax (in methanol) nm (ε):
  213 (41700), 286 (29500), 338sh(14900), 429sh(6500)
Infrared Absorption Spectrum νmax (KBr) $cm^{-1}$:
  3358, 3073, 1700, 1674, 1631, 1464, 1276, 1248
  $^1$H-NMR spectrum:
  Spectrum measured at 500 MHz in hexadeutero dimethylsulfoxide (DMSO-$d_6$) is shown in FIG. 1.
  $^{13}$C-NMR spectrum:
  Spectrum measured at 125 MHz in hexadeutero dimethylsulfoxide (DMSO-$d_6$) is shown in FIG. 2.

Solubility:
  Insoluble in water and hexane, and soluble in methanol and DMSO.
(SPF-3059-16)
Appearance: cream-colored powder
Molecular weight: 580
Molecular formula: $C_{28}H_{20}O_{14}$
Fast Atom Bombardment Mass Spectrum (FAB-MS) m/z (positive):
581 $(M+H)^+$
Fast Atom Bombardment Mass Spectrum (FAB-MS) m/z (negative):
579 $(M-H)^-$
High Resolution Fast Atom Bombardment Mass Spectrum (HRFAB-MS) m/z$(M-H)^-$:

Measured value: 579.0812

Calculated value: 579.0776 ($C_{28}H_{19}O_{14}$)

UV-VISIBLE Absorption Spectrum λmax (in methanol) nm (ε):

210 (44500), 323 (15000), 353sh(12000)

Infrared Absorption Spectrum νmax (KBr) cm$^{-1}$:

3420, 1694, 1668, 1634, 1568, 1464, 1278

$^1$H-NMR (DMSO-$d_6$) δppm:

1.88 (3H, s), 2.08 (3H, s), 2.28 (1H, d, 16.6), 2.34 (1H, d, 16.6), 4.07 (1H, d, 10.1), 4.17 (1H, s), 4.42 (1H, d, 10.1), 6.29 (1H, s), 6.93 (1H, s)

$^{13}$C-NMR (DMSO-$d_6$) δppm:

21.1, 24.2, 30.4, 50.1, 50.4, 64.9, 69.3, 102.3, 104.1, 110.6, 111.6, 112, 119.0, 121.6, 138.7, 139.4, 141.6, 147.1, 148.0, 150.4, 152.1, 160.4, 162.6, 167.7, 171.3, 174.3, 198.6, 201.3

Solubility:

Insoluble in water and hexane, and soluble in methanol and DMSO.

Taken together, the structure of SPF-3059-16 was determined as the following formula (steric configuration is a relative configuration):

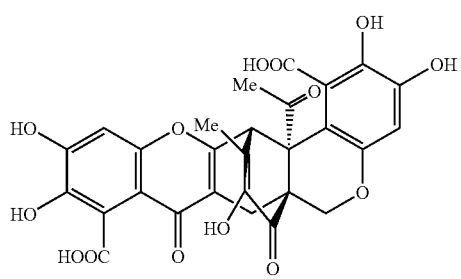

(SPF-3059-17)

Appearance: yellow powder

Molecular weight: 578

Molecular formula: $C_{28}H_{18}O_{14}$

Fast Atom Bombardment Mass Spectrum (FAB-MS) m/z (positive):

579 (M+H)$^+$

Fast Atom Bombardment Mass Spectrum (FAB-MS) m/z (negative):

577 (M−H)$^-$

High Resolution Fast Atom Bombardment Mass Spectrum (HRFAB-MS) m/z(M−H)$^-$:

Measured value: 577.0675

Calculated value: 577.0619 ($C_{28}H_{17}O_{14}$)

UV-VISIBLE Absorption Spectrum λmax (in methanol) nm (ε):

214 (49400), 301 (8900), 390 (22100)

Infrared Absorption Spectrum νmax (KBr) cm$^{-1}$:

3109, 1656, 1564, 1459, 1272

$^1$H-NMR (DMSO-$d_6$) δppm:

1.89 (3H, s), 2.46 (3H, s), 4.85 (1H, d, 13.3), 4.92 (1H, d, 13.3), 5.52 (1H, s), 6.42 (1H, s), 6.65 (1H, s), 6.88 (1H, s)

$^{13}$C-NMR (DMSO-$d_6$) δppm:

17.1, 20.2, 61.9, 71.9, 91.8, 102.8, 103.0 (2C), 103.5, 111.0, 112.6, 117.6, 119.2, 122.9, 139.4, 143.3, 149.2, 150.4, 151.2, 151.71 154.4, 159.1, 163.4, 165.6, 167.8, 168.6, 170.9, 172.9

Solubility:

Insoluble in water and hexane, and soluble in methanol and DMSO.

Taken together, the structure of SPF-3059-17 was determined as the following formula:

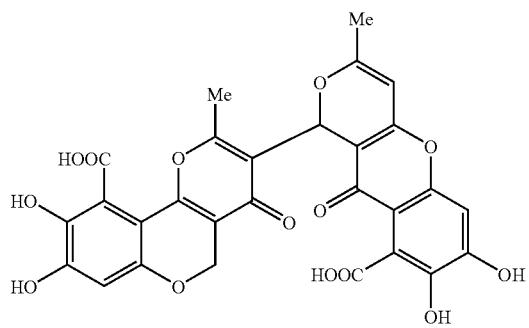

(SPF-3059-18)

Appearance: orange powder

Properties of the substance: acidic substance

Molecular weight: 560

Molecular formula: $C_{28}H_{16}O_{13}$

Fast Atom Bombardment Mass Spectrum (FAB-MS) m/z (positive):

561 (M+H)$^+$

Fast Atom Bombardment Mass Spectrum (FAB-MS) m/z (negative):

559 (M−H)$^-$

High Resolution Fast Atom Bombardment Mass Spectrum (HRFAB-MS) m/z(M+H)$^+$:

Measured value: 561.0710

Calculated value: 561.0670 ($C_{28}H_{17}O_{13}$)

UV-VISIBLE Absorption Spectrum λmax (in methanol) nm (ε):

219 (34300), 257 (28900), 311 (28600), 404 (14600), 450 (14400)

Infrared Absorption Spectrum νmax (KBr) cm$^{-1}$:

3154, 1657, 1605, 1468, 1279

Figure 3:
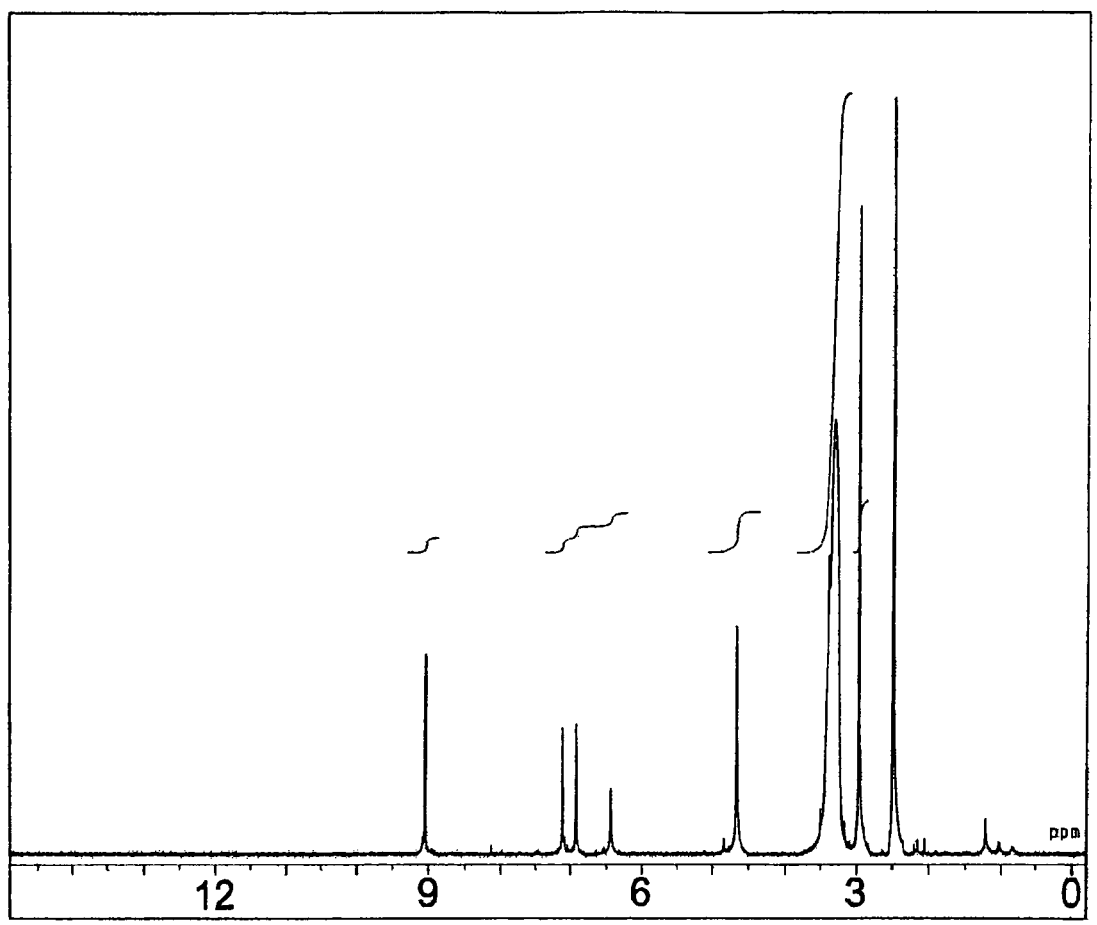
FIG. 3 shows a $^1$H-NMR spectrum (DMSO-$d_6$) of SPF-3059-18.

$^1$H-NMR spectrum:

Spectrum measured at 500 MHz in hexadeutero dimethylsulfoxide (DMSO-$d_6$) is shown in FIG. 3.

Figure 4:
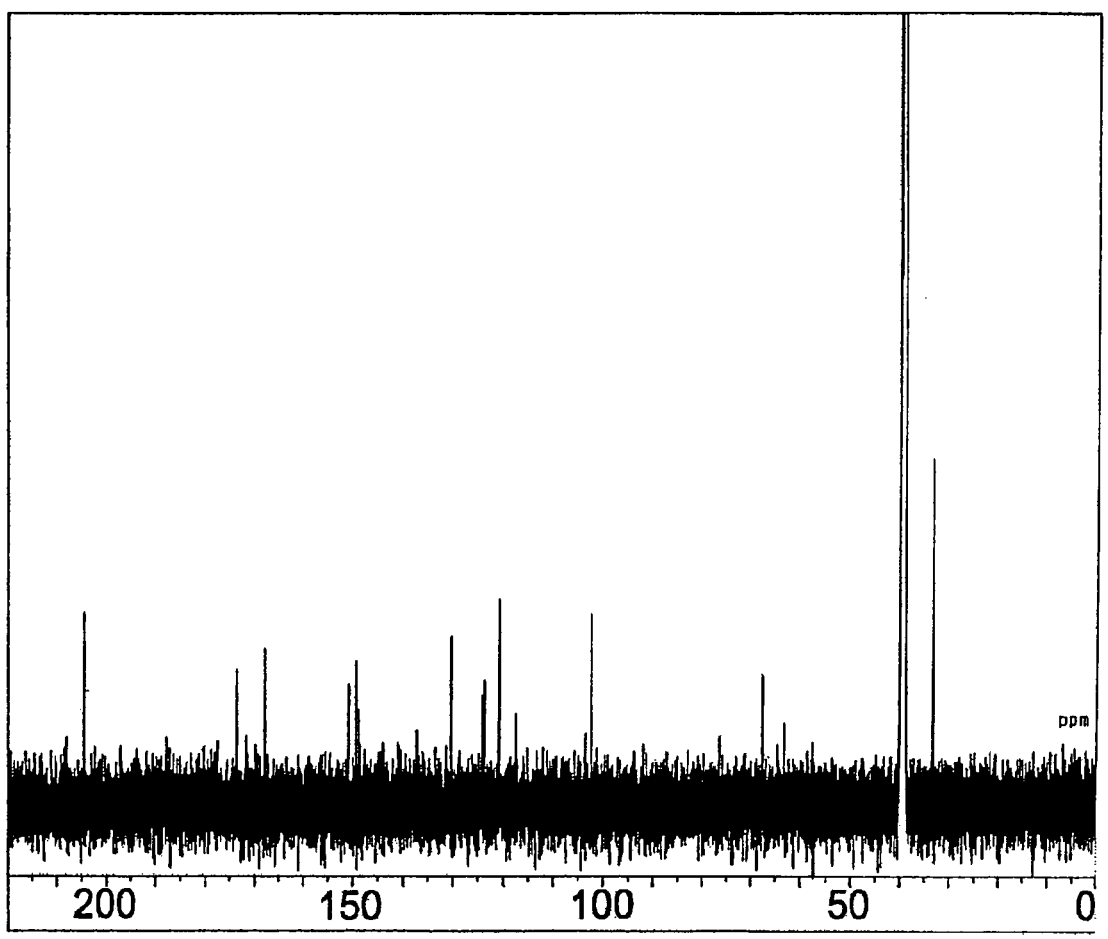
FIG. 4 shows a $^{13}$C-NMR spectrum (DMSO-$d_6$) of SPF-3059-18.

$^{13}$C-NMR spectrum:

Spectrum measured at 125 MHz in hexadeutero dimethylsulfoxide (DMSO-$d_6$) is shown in FIG. 4.

Solubility:

Insoluble in water and hexane, and soluble in methanol and DMSO.

(SPF-3059-19)

Appearance: yellow powder

Molecular weight: 596

Molecular formula: $C_{28}H_{20}O_{15}$

Fast Atom Bombardment Mass Spectrum (FAB-MS) m/z (positive):

597 (M+H)$^+$

Fast Atom Bombardment Mass Spectrum (FAB-MS) m/z (negative):

595 (M−H)$^-$

High Resolution Fast Atom Bombardment Mass Spectrum (HRFAB-MS) m/z(M−H)$^-$:

Measured value: 597.0890

Calculated value: 597.0881 ($C_{28}H_{21}O_{15}$)

UV-VISIBLE Absorption Spectrum λmax (in methanol) nm (ε):
204 (34600), 225 (30900), 267sh(8300), 319 (17100), 349 (13800), 404 (10100)

Infrared Absorption Spectrum νmax (KBr) cm$^{-1}$:
3418, 1634, 1605, 1462, 1270

$^1$H-NMR (DMSO-d$_6$) δppm:
1.43 (3H, s), 1.55 (3H, s), 2.94 (1H, d, 5.5), 3.17 (1H, d, 18.6), 3.24 (1H, d, 18.6), 4.38 (1H, d, 11.9), 4.54 (1H, d, 11.9), 5.27 (1H, d, 5.5), 5.84 (1H, s), 6.59 (1H, s)

$^{13}$C -NMR (DMSO-d$_6$) δppm:
24.5, 28.7, 36.6, 49.4, 62.1, 64.2, 96.8, 99.6, 102.0, 102.6, 103.0, 104.0, 111.1, 120.2 (2C), 113.1, 137.3, 146.5, 150.8, 151.8, 152.0, 153.0, 159.2, 161.3, 167.7, 169.8, 172.6, 185.4

Solubility:
Insoluble in water and hexane, and soluble in methanol and DMSO.

Taken together, the structure of SPF-3059-19 was determined as the following formula:

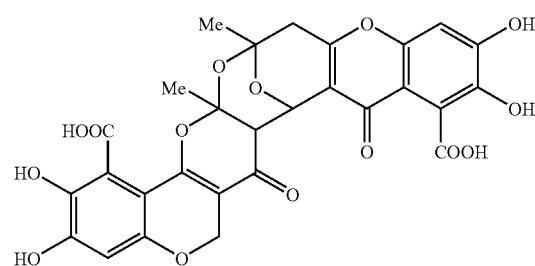

(SPF-3059-20)
Appearance: yellow powder
Molecular weight: 562
Molecular formula: C$_{28}$H$_{18}$O$_{13}$
Fast Atom Bombardment Mass Spectrum (FAB-MS) m/z (positive):
563 (M+H)$^+$
Fast Atom Bombardment Mass Spectrum (FAB-MS) m/z (negative):
561 (M−H)$^-$
0High Resolution Fast Atom Bombardment Mass Spectrum (HRFAB-MS) m/z(M−H)$^-$:
Measured value: 563.0882
Calculated value: 563.0826 (C$_{28}$H$_{19}$O$_{13}$)
UV-VISIBLE Absorption Spectrum λmax (in methanol) nm (ε):
216 (49100), 301 (21700), 369 (14200)
Infrared Absorption Spectrum νmax (KBr) cm$^{-1}$:
3444, 3069, 1690, 1649, 1619, 1536, 1435, 1283
$^1$H-NMR (DMSO-d$_6$) δppm:
1.76 (3H, s), 2.21 (3H, s), 3.09 (1H, d, 18.8), 3.43 (1H, d, 18.8), 4.75 (1H, d, 13.4), 5.03 (1H, d, 13.4), 6.17 (1H, s), 6.18 (1H, s), 6.75 (1H, d, 2.1), 6.83 (1H, d, 2.1)

$^{13}$C-NMR (DMSO-d$_6$) δppm:
18.7, 27.0, 38.3, 61.8, 62.2, 101.0, 102.9, 104.8, 112.3, 112.7, 113.1, 113.3, 113.4, 117.4, 119.2, 136.3, 141.1, 143.7, 145.1, 154.7, 156.9, 160.2, 161.9, 164.7, 167.3, 169.3, 170.8, 174.9

Solubility:
Insoluble in water and hexane, and soluble in methanol and DMSO.

Taken together, the structure of SPF-3059-20 was determined as the following formula:

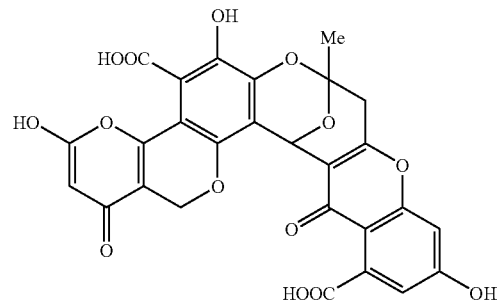

(SPF-3059-22)
Appearance: cream-colored powder
Molecular weight: 548
Molecular formula: C$_{27}$H$_{16}$O$_{13}$
Fast Atom Bombardment Mass Spectrum (FAB-MS) m/z (positive):
549 (M+H)$^+$
Fast Atom Bombardment Mass Spectrum (FAB-MS) m/z (negative):
547 (M−H)$^-$
High Resolution Fast Atom Bombardment Mass Spectrum (HRFAB-MS) m/z(M+H)$^+$:
Measured value: 547.0568
Calculated value: 547.0513 (C$_{27}$H$_{15}$O$_{13}$)
UV-VISIBLE Absorption Spectrum λmax (in methanol) nm (ε):
208 (51900), 240sh(43900), 270sh(38000), 310 (30700), 387 (18000)
Infrared Absorption Spectrum νmax (KBr) cm$^{-1}$:
3410, 3068, 1655, 1619, 1599, 1561, 1460, 1310, 1251
$^1$H-NMR (DMSO-d$_6$) δppm:
2.34 (3H, s), 2.73 (3H, s), 6.31 (1H, s), 6.98 (1H, s), 8.08 (1H, s) 8.69 (1H, s)

$^{13}$C-NMR (DMSO-d$_6$) δppm:
17.1, 32.3, 98.1, 101.8, 102.6, 113.3, 117.1, 119.8, 123.2, 125.4, 126, 131.9, 136.2, 140.4, 142.1, 144.7, 150.4, 152.7, 152.9, 154.8, 156.2, 160.4, 167.1, 172.1, 178.9, 192.7, 202.4

Solubility:
Insoluble in water and hexane, and soluble in methanol and DMSO.

Taken together, the structure of SPF-3059-22 was determined as the following formula:

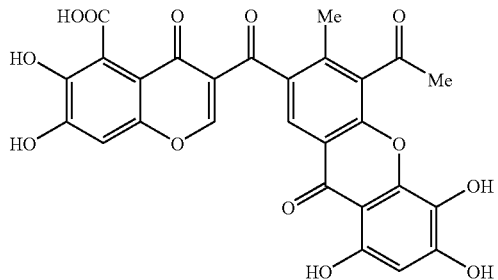

(SPF-3059-23)
Appearance: yellow powder
Molecular weight: 686
Molecular formula: $C_{34}H_{22}O_{16}$
Fast Atom Bombardment Mass Spectrum (FAB-MS) m/z (positive):
687 $(M+H)^+$
Fast Atom Bombardment Mass Spectrum (FAB-MS) m/z (negative):
685 $(M-H)^-$
High Resolution Fast Atom Bombardment Mass Spectrum (HRFAB-MS) m/z$(M+H)^+$:
Measured value: 685.0887
Calculated value: 685.0830 ($C_{34}H_{21}O_{16}$)
UV-VISIBLE Absorption Spectrum λmax (in methanol) nm (ε):
213 (53800), 282sh(24100), 324 (21700)
Infrared Absorption Spectrum νmax (KBr) cm$^{-1}$:
3354, 1688, 1588, 1468, 1288
$^1$H-NMR (DMSO-$d_6$) δppm:
2.14 (3H, s), 2.21 (3H, s), 2.61 (3H, brs), 6.50 (1H, s), 6.85 (1H, s), 7.28 (1H, brs), 7.68 (1H, brs), 8.29 (1H, s)
$^{13}$C-NMR (DMSO-$d_6$) δppm:
30.2, 31.3, 32.3, 102.4, 107.3, 110.0, 114.7, 114.9, 119.7, 120.5, 123.8, 125.9, 126.4, 126.5, 132.6, 135.6, 136.1, 136.7, 139.5, 141.0, 143.4, 145.6, 147.8, 150.4, 151.8, 154.1, 160.5, 167.5, 170.5, 172.7, 197.9, 200.4, 201.2, 202.0

Solubility:
Insoluble in water and hexane, and soluble in methanol and DMSO.

Taken together, the structure of SPF-3059-23 was determined as the following formula:

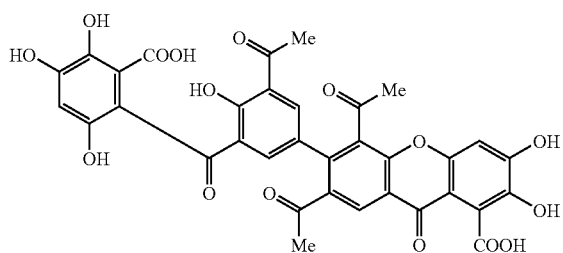

Figure 5:
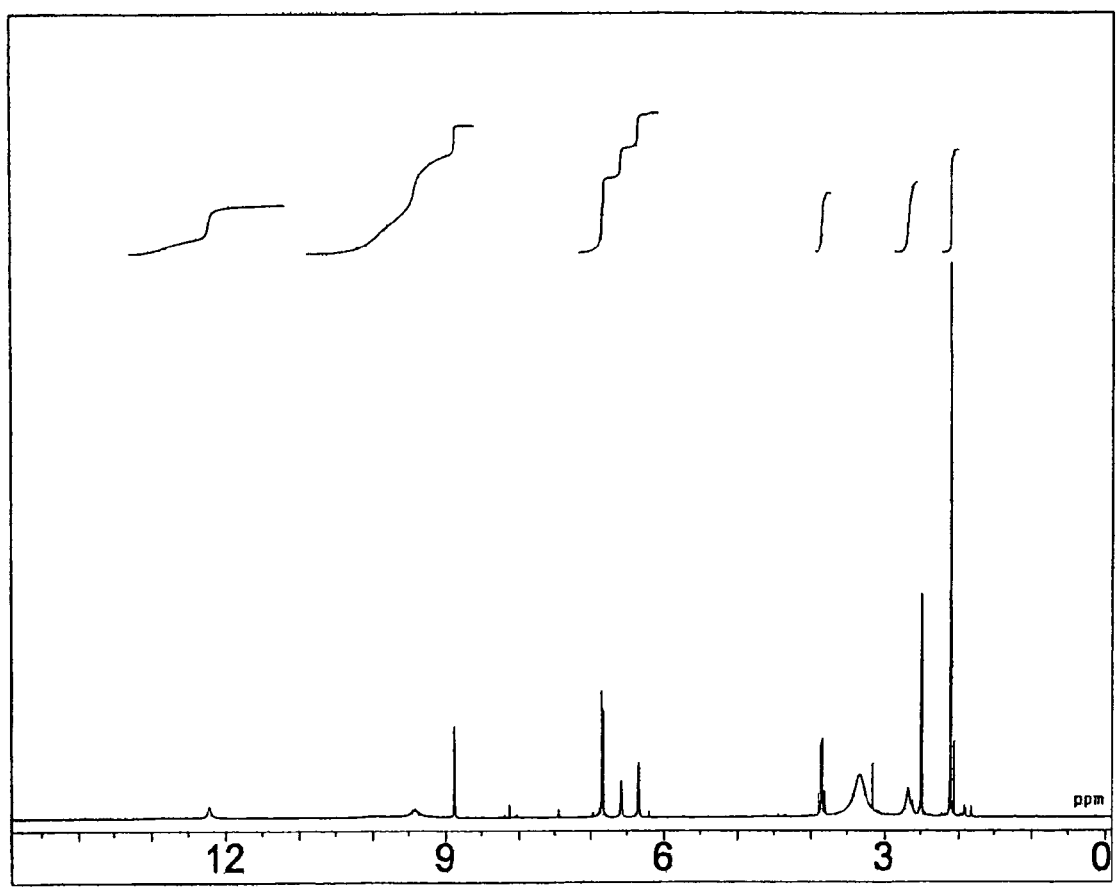
FIG. 5 shows a $^1$H-NMR spectrum (DMSO-$d_6$) of SPF-3059-31.
Figure 6:
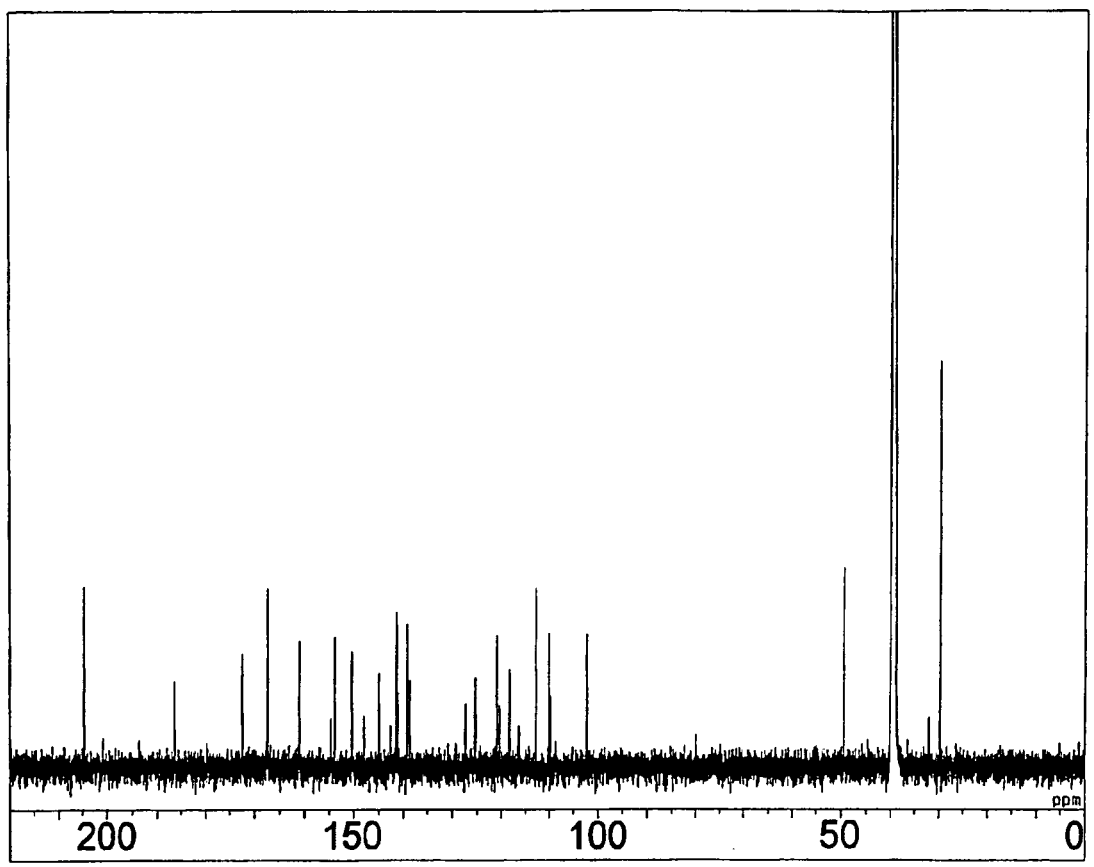
FIG. 6 shows a $^{13}$C-NMR spectrum (DMSO-$d_6$) of SPF-3059-31.

(SPF-3059-31)
Appearance: yellow powder
Properties of the substance: acidic substance
Molecular weight: 668
Molecular formula: $C_{34}H_{20}O_{15}$
Fast Atom Bombardment Mass Spectrum (FAB-MS) m/z (positive):
669 $(M+H)^+$
Fast Atom Bombardment Mass Spectrum (FAB-MS) m/z (negative):
667 $(M-H)^-$
High Resolution Fast Atom Bombardment Mass Spectrum (HRFAB-MS) m/z$(M+H)^+$:
Measured value: 669.0887
Calculated value: 669.0881 ($C_{34}H_{21}O_{15}$)
UV-VISIBLE Absorption Spectrum λmax (in methanol) nm (ε):
213 (54600), 235sh(39400), 312 (31300), 350 (24200)
Infrared Absorption Spectrum νmax (KBr) cm$^{-1}$:
3348, 1766, 1707, 1644, 1588, 1464, 1301
$^1$H-NMR:
Spectrum measured at 500 MHz in hexadeutero dimethylsulfoxide (DMSO-$d_6$) is shown in FIG. 5.
$^{13}$C-NMR:
Spectrum measured at 125 MHz in hexadeutero dimethylsulfoxide (DMSO-$d_6$) is shown in FIG. 6.

Solubility:
Insoluble in water and hexane, and soluble in methanol and DMSO.

(SPF-3059-38)
Appearance: yellow powder
Molecular weight: 654
Molecular formula: $C_{34}H_{22}O_{14}$
Fast Atom Bombardment Mass Spectrum (FAB-MS) m/z (positive):
655 $(M+H)^+$
Fast Atom Bombardment Mass Spectrum (FAB-MS) m/z (negative):
653 $(M-H)^-$
High Resolution Fast Atom Bombardment Mass Spectrum (HRFAB-MS) m/z$(M+H)^+$:
Measured value: 655.1100
Calculated value: 655.1088 ($C_{34}H_{23}O_{14}$)
UV-VISIBLE Absorption Spectrum λmax (in methanol) nm (ε):
212 (41100), 239sh(34000), 287 (22200), 300sh(21900), 328 (24400)
Infrared Absorption Spectrum νmax (KBr) cm$^{-1}$:
3418, 1696, 1660, 1607, 1471, 1283
$^1$H-NMR (DMSO-$d_6$) δppm:
2.30 (1H, m), 2.36 (1H, m), 2.65 (3H, s), 2.81 (1H, m), 2.96 (1H, m), 3.00 (3H, s), 4.56 (1H, d, 11.8), 4.75 (1H, d, 11.8), 6.43 (1H, s), 7.07 (1H, s), 8.15 (1H, d, 9.2), 8.73 (1H, d, 9.2)
$^{13}$C-NMR (DMSO-$d_6$) δppm: 21.7, 23.3, 26.6, 32.9, 56.9, 71.3, 102.3, 102.5, 107.9, 110.2, 117.4, 119.4, 121.2, 122.22, 122.24, 124.0, 127.1, 134.3, 136.1, 138.1, 141.7, 141.8, 142.1, 150.1, 154.0, 154.1, 154.6, 155.6, 167.7, 167.9, 173.1, 189.5, 197.5, 207.2

Solubility:
Insoluble in water and hexane, and soluble in methanol and DMSO.

Taken together, the structure of SPF-3059-38 was determined as the following formula:

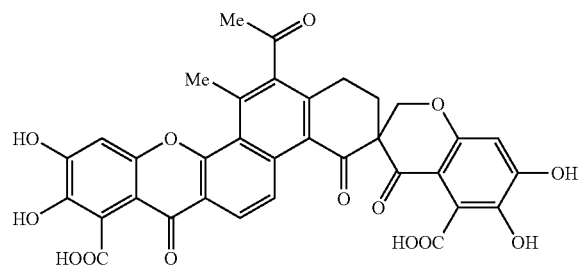

(SPF-3059-40)
Appearance: orange powder
Molecular weight: 536
Molecular formula: $C_{27}H_{20}O_{12}$
Fast Atom Bombardment Mass Spectrum (FAB-MS) m/z (positive):
537 (M+H)$^+$
Fast Atom Bombardment Mass Spectrum (FAB-MS) m/z (negative):
535 (M−H)$^−$
High Resolution Fast Atom Bombardment Mass Spectrum (HRFAB-MS) m/z(M+H)$^+$:
Measured value: 537.1018
Calculated value: 537.1034 ($C_{27}H_{21}O_{12}$)
UV-VISIBLE Absorption Spectrum λmax (in methanol) nm (ε):
209 (34100), 223 (34200), 277 (19900), 340 (11600), 460 (25000)
Infrared Absorption Spectrum νmax (KBr) cm$^{-1}$:
3361, 1698, 1620, 1465, 1293
$^1$H-NMR (DMSO-d$_6$) δppm:
1.95 (3H, s), 2.34 (1H, d, 16.8), 2.63 (3H, s), 3.22 (1H, d, 16.8), 4.04 (1H, d, 10.8), 4.51 (1H, d, 10.8), 5.78 (1H, s), 6.27 (1H, s), 6.76 (1H, s), 6.78 (1H, s)
$^{13}$C-NMR (DMSO-d$_6$) δppm:
23.7, 24.4, 32.0, 50.6, 71.9, 98.4, 102.5, 104.5, 109.0, 109.3, 111.9, 112.7, 118.8, 125.0, 135.4, 141.2, 143.0, 149.7, 151.1, 152.0, 152.6, 155.8, 168.3, 172.5, 189.0, 197.0, 204.2

Solubility:
Insoluble in water and hexane, and soluble in methanol and DMSO.

Taken together, the structure of SPF-3059-40 was determined as the following formula:

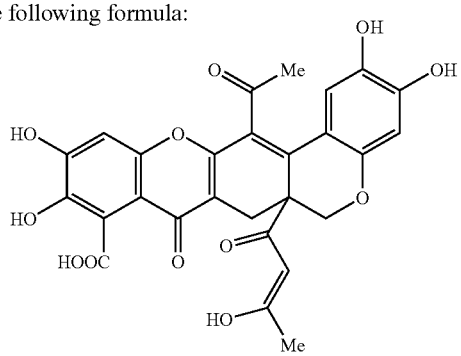

Figure 7:
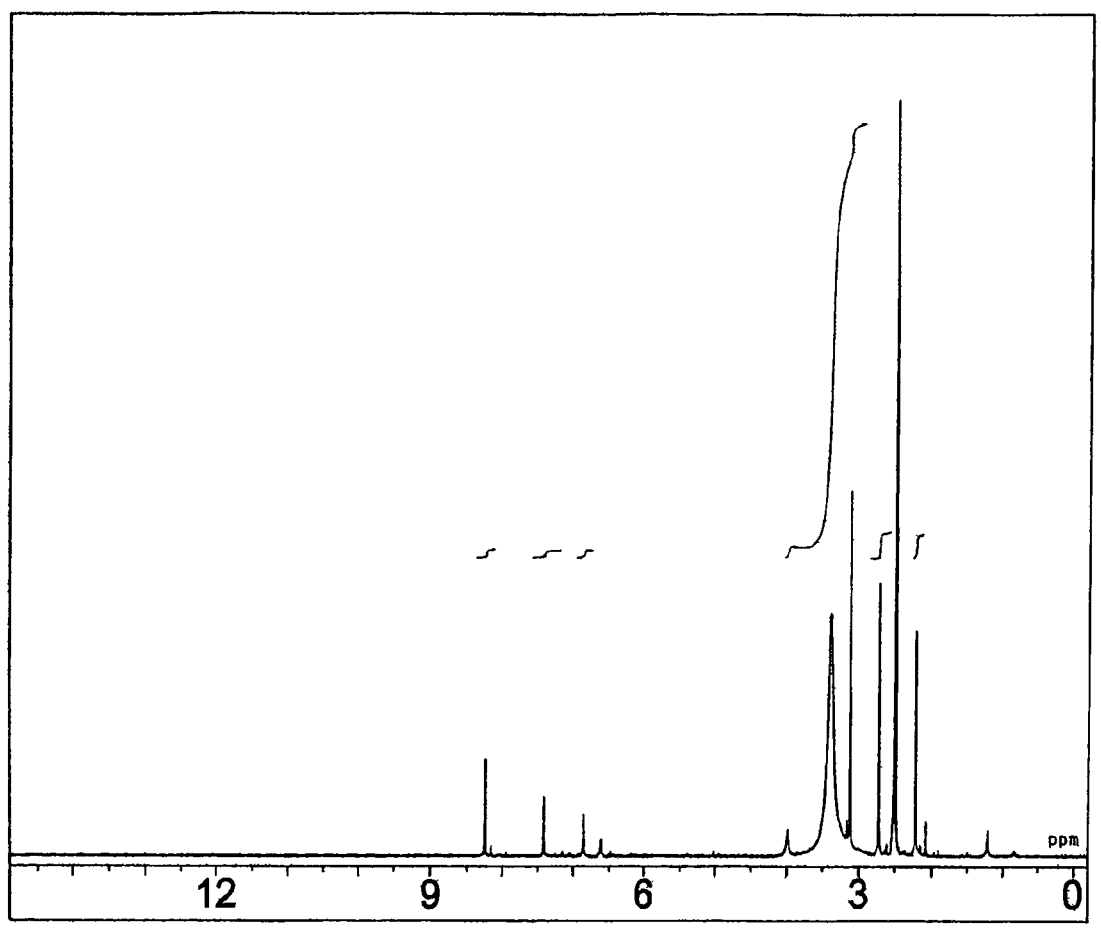
FIG. 7 shows a $^1$H-NMR spectrum (DMSO-$d_6$) of SPF-3059-41.
Figure 8:
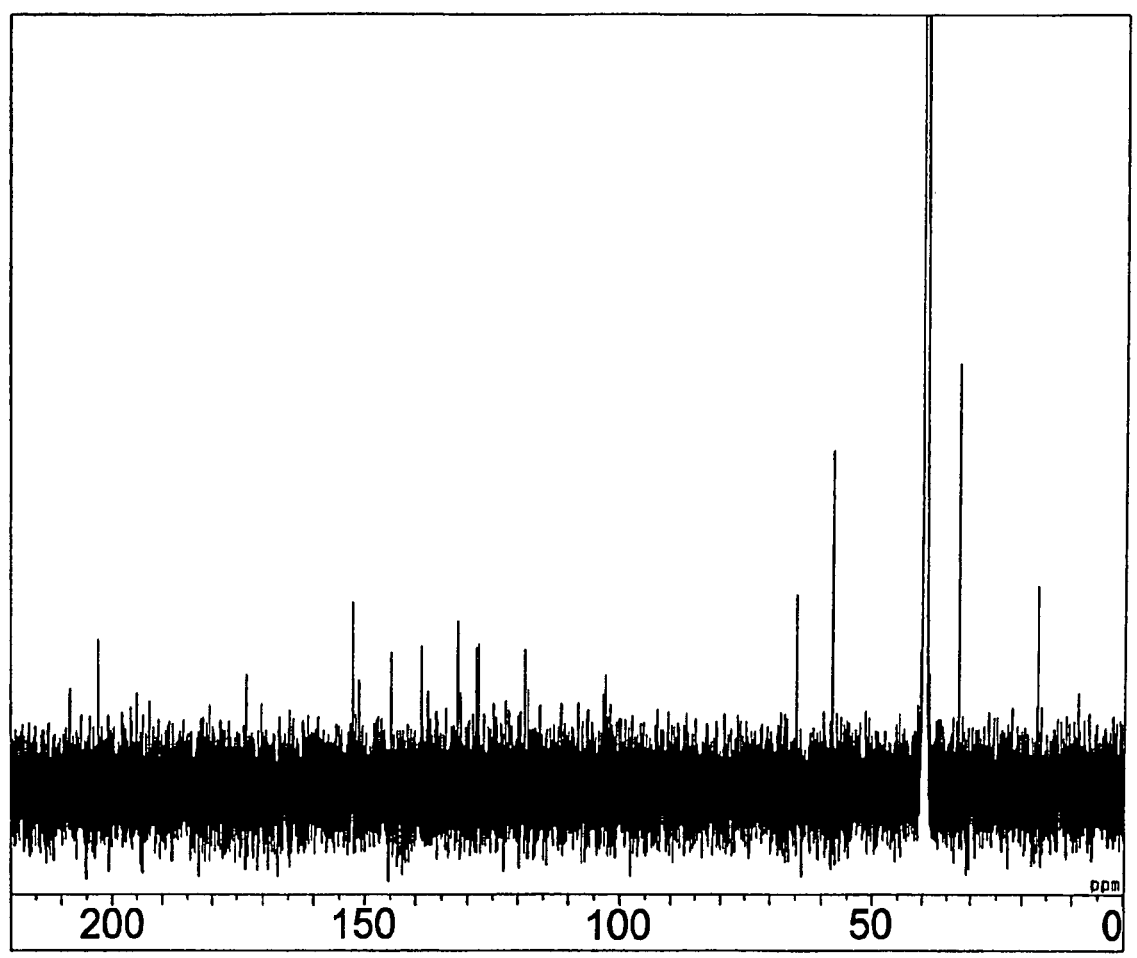
FIG. 8 shows a $^{13}$C-NMR spectrum (DMSO-$d_6$) of SPF-3059-41.

(SPF-3059-41)
Appearance: yellow powder
Properties of the substance: acidic substance
Molecular weight: 548
Molecular formula: $C_{28}H_{20}O_{12}$
Fast Atom Bombardment Mass Spectrum (FAB-MS) m/z (positive):
549 (M+H)$^+$
Fast Atom Bombardment Mass Spectrum (FAB-MS) m/z (negative):
547 (M−H)$^−$
High Resolution Fast Atom Bombardment Mass Spectrum (HRFAB-MS) m/z(M+H)$^+$:
Measured value: 549.1002
Calculated value: 549.1034 ($C_{28}H_{21}O_{12}$)
UV-VISIBLE Absorption Spectrum λmax (in methanol) nm (ε):
227 (30200), 282sh(13500), 315 (13900), 356 (11000)
Infrared Absorption Spectrum νmax (KBr) cm$^{-1}$:
3396, 1688, 1662, 1622, 1470, 1294
$^1$H-NMR spectrum:
Spectrum measured at 500 MHz in hexadeutero dimethyl-sulfoxide (DMSO-d$_6$) is shown in FIG. 7.
$^{13}$C-NMR spectrum:
Spectrum measured at 125 MHz in hexadeutero dimethyl-sulfoxide (DMSO-d$_6$) is shown in FIG. 8.

Solubility:
Insoluble in water and hexane, and soluble in methanol and DMSO.

(SPF-3059-42)
Appearance: yellow powder
Molecular weight: 806
Molecular formula: $C_{41}H_{26}O_{18}$
Fast Atom Bombardment Mass Spectrum (FAB-MS) m/z (positive):
807 (M+H)$^+$
Fast Atom Bombardment Mass Spectrum (FAB-MS) m/z (negative):
805 (M−H)$^−$
High Resolution Matrix-Assisted Laser Desorption/Ionization
Time-of-Flight(HRMALDI-TOF-MS) m/z(M+H)$^+$:
Measured value: 807.1261
Calculated value: 807.1198 ($C_{41}H_{27}O_{18}$)
UV-VISIBLE Absorption Spectrum λmax (in methanol) nm (ε): 221 (58300), 316 (28000), 353 (23100)
Infrared Absorption Spectrum νmax (KBr) cm$^{-1}$: 3400, 1704, 1651, 1620, 1444, 1294
$^1$H-NMR (DMSO-d$_6$) δppm:
2.08 (3H, s), 2.10 (3H, s), 2.51 (3H, s), 3.47 (1H, d, 15.9), 3.54 (1H, d, 15.9), 4.48 (1H, d, 13.1), 4.65 (1H, d, 13.1), 6.28 (1H, s), 6.84 (1H, s), 6.89 (1H, s), 7.40 (1H, s), 8.12 (1H, s)
$^{13}$C-NMR (DMSO-d$_6$) δppm: 16.5, 17.1, 19.1, 31.9, 61.8, 102.1, 102.9 (2C), 103.4, 108.7, 109.2, 111.5, 113.5, 118.5, 119.1 (2C), 119.7, 122.0, 127.8, 128.9, 131.2, 139.1 (2C), 141.7, 144.2, 150.0, 154.0 (2C), 150.5, 150.6, 150.7, 152.0, 152.3, 158.9, 160.9, 167.8, 167.9, 173.1, 173.3, 175.0, 202.5

Solubility:

Insoluble in water and hexane, and soluble in methanol and DMSO.

Taken together, the structure of SPF-3059-42 was determined as the following formula:

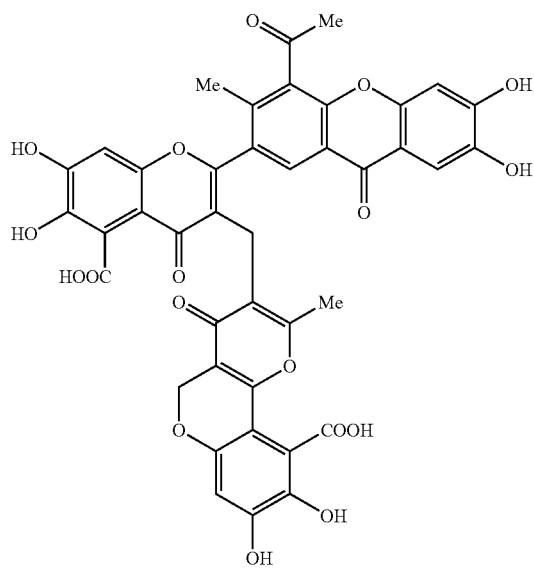

Example 2

Suppressing Action of the Compounds of the Present Invention to the Collapse Activity of Sema3A A 96-well plate (Sumitomo Bakelite Co., Ltd.) pre-coated with polylysine was further coated with laminine (20 μg/ml of laminine, for 1 hour at room temperature). Each well was added with 100 μl of medium (F12 medium containing 10% bovine fetal serum, 20 ng/ml of NGF, 100 units/ml of penicillin and 100 μg/ml of streptomycin) which medium was then inoculated with dorsal root nerve ganglions excised from E7 (Embryonic day 7) chick embryo and cultured for 16 to 20 hours under 5% $CO_2$ at 37° C. Subsequently, the object compounds were added to media at various concentrations and 3 units/ml of mouse semaphorin 3A (Sema3A) was added after cultivating for 1 hour. The cultures were further incubated for another 1 hour. Glutaraldehyde was quickly added therein after said 1 hour to make the final concentration 1%. The cultures were then left for 15 minutes at room temperature so that the tissue sections were fixed, and collapse rates of the growth cones were microscopically determined. IC50 values was defined as a concentration of each compound at which concentration the collapse rate C equals to(A+B)/2, wherein (A) % is the collapse rate of growth cone of the negative control group (neither compounds nor Sema3A was added); (B) % is the collapse rate of growth cone of the positive control group (compounds were not added but Sema3A was added); and (C) % is the collapse rate of growth cone of the test group (each one compound and Sema3A were added). The results are given below. These results reveal that the compounds of the present invention strongly inhibit semaphorin.

TABLE 2

| compound | IC50 (μg/ml) |
|---|---|
| SPF-3059-8 | 2 |
| SPF-3059-10 | 2 |
| SPF-3059-16 | 0.5 |
| SPF-3059-17 | 0.13 |
| SPF-3059-18 | 0.063 |
| SPF-3059-19 | 0.5 |
| SPF-3059-20 | 4 |
| SPF-3059-22 | 0.5 |
| SPF-3059-23 | 0.5 |
| SPF-3059-31 | 0.25 |
| SPF-3059-38 | 0.013 |
| SPF-3059-40 | 0.125 |
| SPF-3059-41 | 0.25 |
| SPF-3059-42 | 0.063 |

Example 3

Production of Salts of the Compounds of the Present Invention

A compound of the present invention is dissolved in methanol to prepare 1 mM solution. Methanol solution of 1 mM sodium hydroxide is added to 1 ml of the above solution by 2 ml when the compound of the present invention has two carboxyl groups, or by 1 ml when it has one carboxyl group, and is mixed thoroughly. Then, solvent of the solution is evaporated under reduced pressure and the residues are dried. Thus 1 μmol of sodium salt of the compound of the present invention is obtained.

INDUSTRIAL APPLICABILITY

The compounds of the present invention have semaphorin inhibitory activity and advantageously used as a preventive or remedy for various neuropathic and neurodegenerative diseases.

The invention claimed is:

1. A compound represented by the general formula (1):

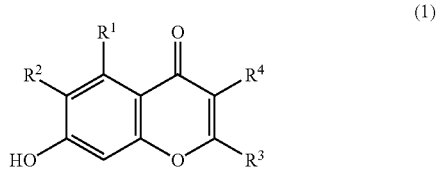

wherein $R^1$, $R^2$, $R^3$ and $R^4$ represent one of the following [I] to [IX]:

[I] $R^1$ represents a hydrogen atom or a carboxyl group, $R^2$ represents a hydrogen atom or a hydroxyl group, and $R^3$ and $R^4$ are joined to form a divalent group of the formula (2):

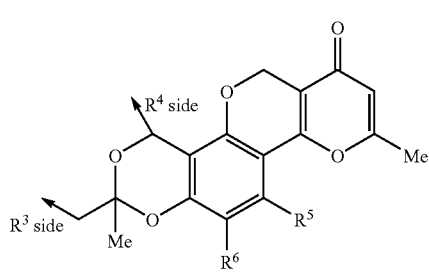

wherein $R^5$ represents a hydrogen atom or a carboxyl group and $R^6$ represents a hydrogen atom or a hydroxyl group;

[II] $R^1$ represents a hydrogen atom or a carboxyl group, $R^2$ represents a hydrogen atom or a hydroxyl group, and $R^3$ and $R^4$ are joined to form a divalent group of the formula (3):

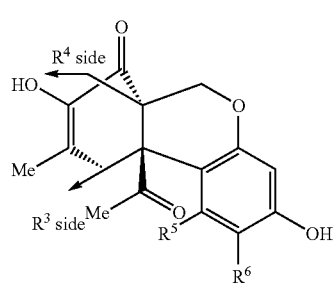

wherein $R^5$ and $R^6$ have the same meanings as above;

[III] $R^1$ represents a hydrogen atom or a carboxyl group, represents a hydrogen atom or a hydroxyl group, and $R^3$ and $R^4$ are joined to form a divalent group of the formula (4):

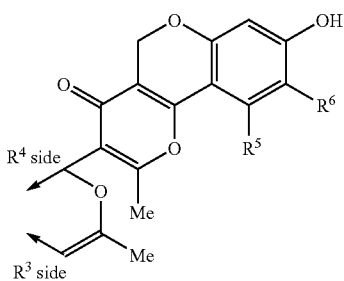

wherein $R^5$ and $R^6$ have the same meanings as above;

[IV] $R^1$ represents a hydrogen atom or a carboxyl group, $R^2$ represents a hydrogen atom or a hydroxyl group, and $R^3$ and $R^4$ are joined to form a divalent group of the formula (5):

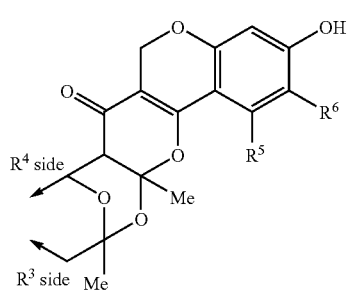

wherein $R^5$ and $R^6$ have the same meanings as above;

[V] $R^1$ represents a hydrogen atom or a carboxyl group, $R^2$ represents a hydrogen atom or a hydroxyl group, and $R^3$ represents a hydrogen atom and $R^4$ represents a group of the formula (6):

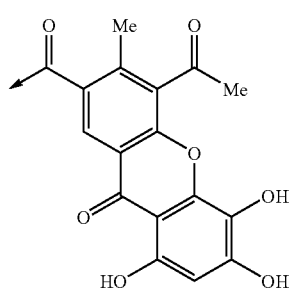

[VI] $R^1$ represents a hydrogen atom or a carboxyl group, $R^2$ represents a hydrogen atom or a hydroxyl group, and $R^3$ and $R^4$ are joined to form a divalent group of the formula (7):

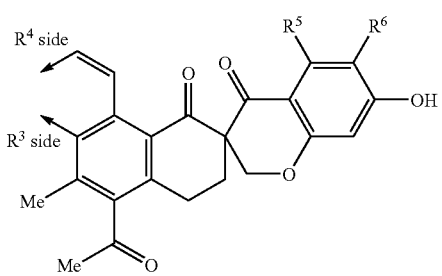

wherein $R^5$ and $R^6$ have the same meanings as above;

[VII] $R^1$ represents a hydrogen atom or a carboxyl group, $R^2$ represents a hydrogen atom or a hydroxyl group, and $R^3$ represents a group of the formula (8):

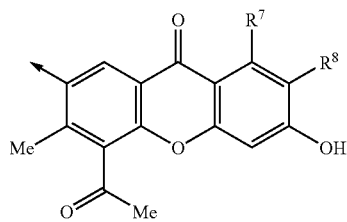
(8)

wherein $R^7$ represents a hydrogen atom or a carboxyl group and $R^8$ represents a hydrogen atom or a hydroxyl group, and $R^4$ represents a group of the formula (9):

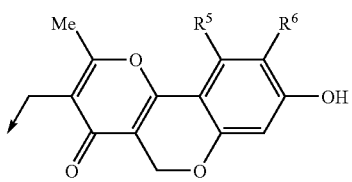
(9)

wherein $R^5$ represents a carboxyl group and $R^6$ has the same meaning as above;

[VIII] $R^1$ represents a carboxyl group, $R^2$ represents a hydroxyl group, and $R^3$ and $R^4$ are joined to form a divalent group of the formula (10):

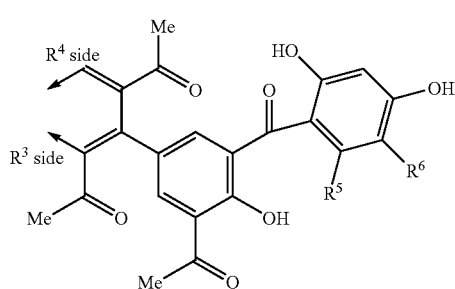
(10)

wherein $R^5$ represents a carboxyl group and $R^6$ represents a hydroxyl group;

[IX] $R^1$ represents a carboxyl group, $R^2$ represents a hydroxyl group, and $R^3$ and $R^4$ are joined to form a divalent group of the formula (11):

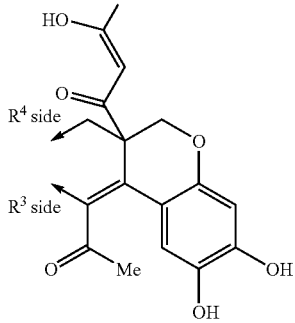
(11)

or a pharmaceutically acceptable salt thereof.

2. The compound according to claim 1 represented by the general formula (12):

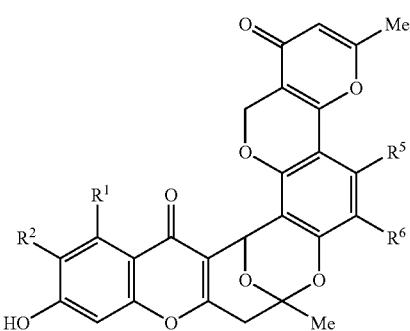
(12)

wherein $R^1$, $R^2$, $R^5$ and $R^6$ have the same meanings as in claim 1 [I], or a pharmaceutically acceptable salt thereof.

3. The compound according to claim 2, wherein $R^1$ and $R^5$ are each a carboxyl group, $R^2$ is a hydroxyl group or a hydrogen atom and $R^6$ is a hydroxyl group in the general formula (12), or a pharmaceutically acceptable salt thereof.

4. The compound according to claim 1 represented by the general formula (13):

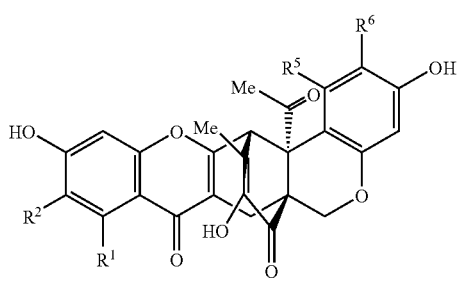
(13)

wherein $R^1$, $R^2$, $R^5$ and $R^6$ have the same meanings as in claim 1 [II], or a pharmaceutically acceptable salt thereof.

5. The compound according to claim 4, wherein $R^1$ and $R^5$ are each a carboxyl group, and $R^2$ and $R^6$ are each a hydroxyl group in the general formula (13), or a pharmaceutically acceptable salt thereof.

6. The compound according to claim 1 represented by the general formula (14):

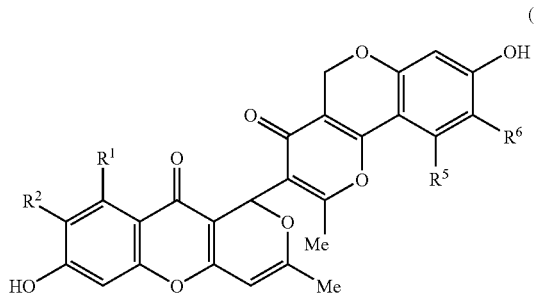

(14)

wherein $R^1$, $R^2$, $R^5$ and $R^6$ have the same meanings as in claim 1 [III], or a pharmaceutically acceptable salt thereof.

7. The compound according to claim 6, wherein $R^1$ and $R^5$ are each a carboxyl group, and $R^2$ and $R^6$ are each a hydroxyl group in the general formula (14), or a pharmaceutically acceptable salt thereof.

8. The compound according to claim 1 represented by the general formula (15):

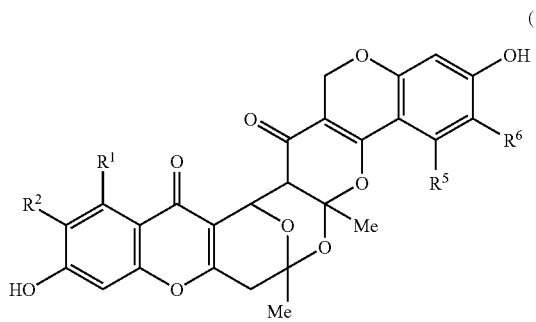

(15)

wherein $R^1$, $R^2$, $R^5$ and $R^6$ have the same meanings as in claim 1 [IV], or a pharmaceutically acceptable salt thereof.

9. The compound according to claim 8, wherein $R^1$ and $R^5$ are each a carboxyl group, and $R^2$ and $R^6$ are each a hydroxyl group in the general formula (15), or a pharmaceutically acceptable salt thereof.

10. The compound according to claim 1 represented by the general formula (16):

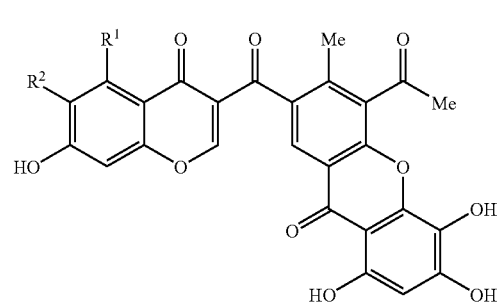

(16)

wherein $R^1$ and $R^2$ have the same meanings as in claim 1 [V], or a pharmaceutically acceptable salt thereof.

11. The compound according to claim 10, wherein $R^1$ represents a carboxyl group and $R^2$ represents a hydroxyl group in the general formula (16), or a pharmaceutically acceptable salt thereof.

12. The compound according to claim 1 represented by the general formula (17):

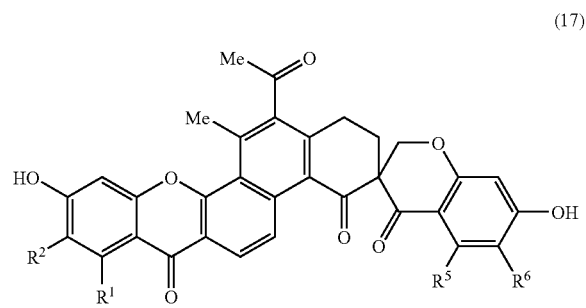

(17)

wherein $R^1$, $R^2$, $R^5$ and $R^6$ have the same meanings as in claim 1 [VI], or a pharmaceutically acceptable salt thereof.

13. The compound according to claim 12, wherein $R^1$ and $R^5$ each represents a carboxyl group, and $R^2$ and $R^6$ each represents a hydroxyl group in the general formula (17), or a pharmaceutically acceptable salt thereof.

14. The compound according to claim 1 represented by the general formula (18):

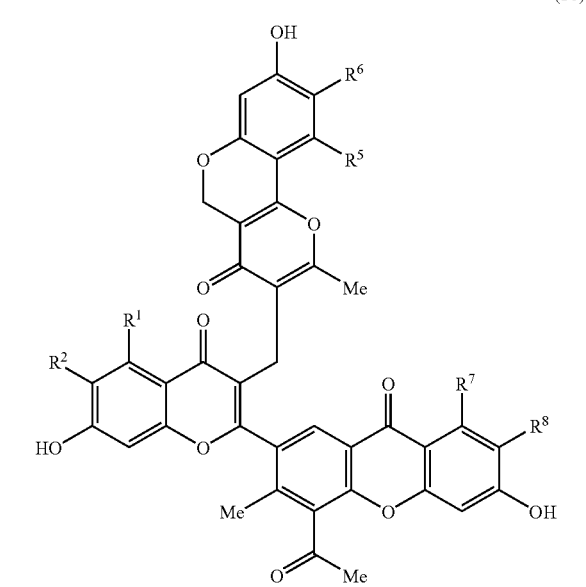

(18)

wherein $R^1$, $R^2$, $R^5$, $R^6$, $R^7$ and $R^8$ have the same meanings as in claim 1 [VII], or a pharmaceutically acceptable salt thereof.

15. The compound according to claim 14, wherein $R^1$ is a carboxyl group, $R^2$, $R^6$ and $R^8$ are each a hydroxyl group, and $R^7$ is a hydrogen atom in the general formula (18), or a pharmaceutically acceptable salt thereof.

16. The compound according to claim 1 represented by the general formula (19):

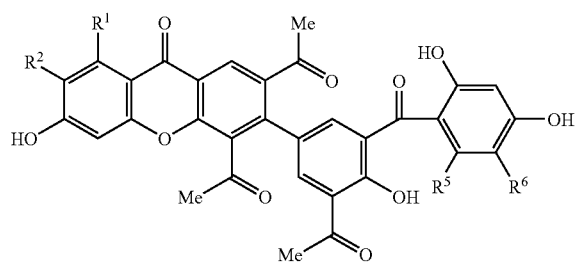

(19)

wherein $R^1$ and $R^5$ each represents a carboxyl group, and $R^2$ and $R^6$ each represents a hydroxyl group, or a pharmaceutically acceptable salt thereof.

17. The compound according to claim 1 represented by the general formula (20):

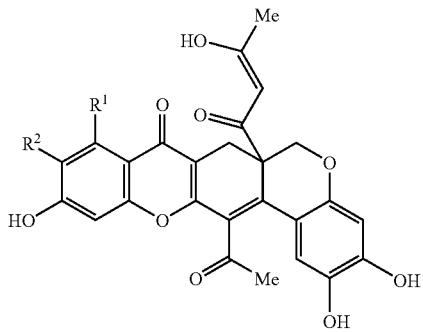

(20)

wherein $R^1$ is a carboxyl group and $R^2$ is a hydroxyl group, or a pharmaceutically acceptable salt thereof.

18. A semaphorin 3A inhibitor comprising as an active ingredient the compound according to claim 1, or a pharmaceutically acceptable salt thereof.

19. A process for producing a compound or a pharmaceutically acceptable salt thereof according to claim 1, wherein the process comprises the steps of: 1) cultivating in a culture medium a microorganism belonging to the genus *Penicillium* which is *Penicillium* sp. SPF-3059 having accession number FERM BP-7663; and 2) collecting the compound according to claim 1 from the culture medium.

20. A method comprising using the compound according to claim 1 or a pharmaceutically acceptable salt thereof as an active ingredient to inhibit semaphorin 3A.

* * * * *